(12) United States Patent
Courtney et al.

(10) Patent No.: US 9,993,590 B2
(45) Date of Patent: Jun. 12, 2018

(54) REAL-TIME ADAPTIVE IMMUNE SYSTEM AND METHOD

(75) Inventors: Angela Courtney, Knights Landing, CA (US); Abigail Spinner, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 673 days.

(21) Appl. No.: 13/980,090

(22) PCT Filed: Jan. 5, 2012

(86) PCT No.: PCT/US2012/020310
§ 371 (c)(1),
(2), (4) Date: Jul. 17, 2013

(87) PCT Pub. No.: WO2012/099721
PCT Pub. Date: Jul. 26, 2012

(65) Prior Publication Data
US 2013/0303960 A1    Nov. 14, 2013

Related U.S. Application Data

(60) Provisional application No. 61/433,859, filed on Jan. 18, 2011.

(51) Int. Cl.
*A61M 37/00* (2006.01)
*A61M 1/36* (2006.01)
(Continued)

(52) U.S. Cl.
CPC ........... *A61M 1/3687* (2013.01); *B82Y 15/00* (2013.01); *C07K 16/2812* (2013.01);
(Continued)

(58) Field of Classification Search
CPC ..... A61M 1/367; A61M 1/3687; B82Y 15/00; C07K 16/2812; C07K 16/2896; G01N 33/56966; G01N 33/56972
See application file for complete search history.

(56) References Cited

U.S. PATENT DOCUMENTS

2005/0003484 A1 * 1/2005 Hirano ................... A61K 39/12
                                                                 435/69.1
2005/0098495 A1    5/2005 Hughes
(Continued)

OTHER PUBLICATIONS

PCT International Search Report, PCT Application No. PCT/US2012/020310, dated Nov. 1, 2012, 10 pages.
(Continued)

*Primary Examiner* — Philip R Wiest
(74) *Attorney, Agent, or Firm* — Fenwick & West LLP

(57) ABSTRACT

The interface between nanotechnology and biological systems is used to synthetically replicate the body's vital, innate, immune functions with targeted precision. Through the creation and use of complexed nanodiamonds (or other particles) with capture agents in a flow-through return apparatus or in an analytic/diagnostic tool, the invention provides individualized treatment of blood-borne pathogens and disease spectrums and rapid, individualized diagnostics. The invention can be used, for example, to clear blood-borne pathogens during initial infections prior to tissue sequestration in real time, to decrease overwhelming numbers of bacterial/viral/cytokine load during life threatening infectious conditions, to super sensitize the immune system to a variety of conditions-cancer markers, vaccinates, etc., to tag and present preloaded microspheres to the immune system for phagocytosis and cell control or delivery, to create human-derived antibodies in vitro for use in vivo, to create direct human anticancer therapies through linkages, among various other areas.

20 Claims, 12 Drawing Sheets

(51) Int. Cl.
 B82Y 15/00 (2011.01)
 C07K 16/28 (2006.01)
 G01N 33/569 (2006.01)
(52) U.S. Cl.
 CPC ... *C07K 16/2896* (2013.01); *G01N 33/56966* (2013.01); *G01N 33/56972* (2013.01)

(56) References Cited

U.S. PATENT DOCUMENTS

| | | | | |
|---|---|---|---|---|
| 2008/0064050 A1* | 3/2008 | Delehanty | ............ | C07D 311/62 435/7.32 |
| 2008/0223776 A1* | 9/2008 | Sumian | ............... | A61M 1/3636 210/257.1 |
| 2009/0192434 A1* | 7/2009 | Thorn | .................... | C07K 16/28 604/6.03 |
| 2010/0298600 A1 | 11/2010 | Lee | | |

OTHER PUBLICATIONS

PCT Invitation to Pay Additional Fees, PCT Application No. PCT/US2012/020310, dated Aug. 31, 2012, 7 pages.
"Real Time Adaptive External Immune System," Dec. 31, 2011, The Regents of the University of California, 2 pages, [Online] [Retrieved on Oct. 18, 2013] Retrieved from the Internet<URL:http://techtransfer.universityofcalifornia.edu/NCD/21394.html>.
Bradac, C. et al., "Prediction and Measurement of the Size-Dependent Stability of Fluorescence in Diamond Over the Entire Nanoscale," Nano Letters, 2009, pp. 3555-3564, vol. 9, No. 10.
Huang, H. et al., "Active Nanodiamond Hydrogels for Chemotherapeutic Delivery," Nano Letters, 2007, pp. 3305-3314, vol. 7, No. 11.
Kulin, S. et al., "Real-Time Measurement of Spontaneous Antigen-Antibody Dissociation," Biophysical Journal, Oct. 2002, pp. 1965-1973, vol. 83.
Leonard, S., "Electrically Conductive Diamond Shows Promise for In Vivo, MEMS Devices," Medical Product Manufacturing News, Oct. 2009, [Online] [Retrieved on Jul. 1, 2014] May be Retrieved at URL<http://www.devicelink.com/mpmn/archive/09/10/002.html>.
Mohan, N. et al., "In Vivo Imaging and Toxicity Assessments of Fluorescent Nanodiamonds in Caenorhabditis Elegans," Nano Letters, Sep. 8, 2010, pp. 3692-3699, vol. 10, No. 9.
Schrand, A. et al., "Nanodiamond Particles: Properties and Perspectives for Bioapplications," Critical Reviews in Solid State and Materials Sciences, 2009, pp. 18-74, vol. 34.
Vandelinger V. et al., "Perfusion in Microfluidic Cross-Flow: Separation of White Blood Cells from Whole Blood and Exchange of Medium in a Continuous Flow," Anal. Chem., 2007, pp. 202-203, vol. 79, No. 5.
Yang, K. et al., "Preparation of DNA-Encapsulated Polyethersulfone Hollow Microspheres for Organic Compounds and Heavy Metal Ions Removal," Desalination, May 30, 2005, pp. 297-302, vol. 175, No. 3.

* cited by examiner

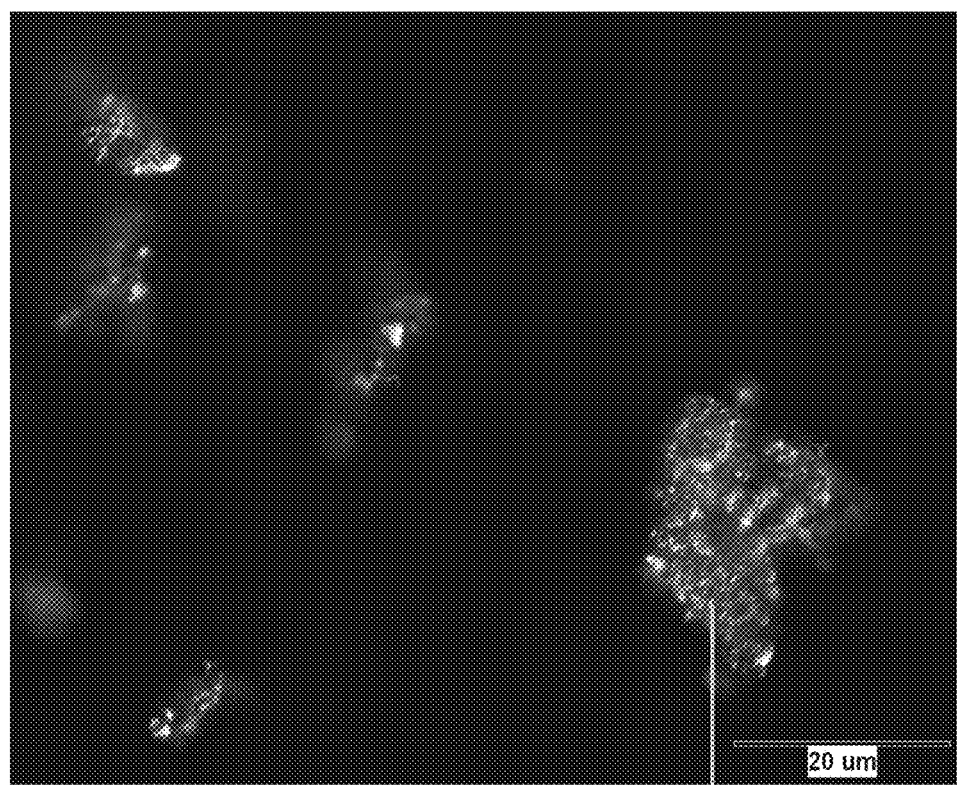
FIG. 1  Nanodiamond

FIG. 5 Nanodiamond conjugated with an FITC mouse anti-monkey CD4 antibody
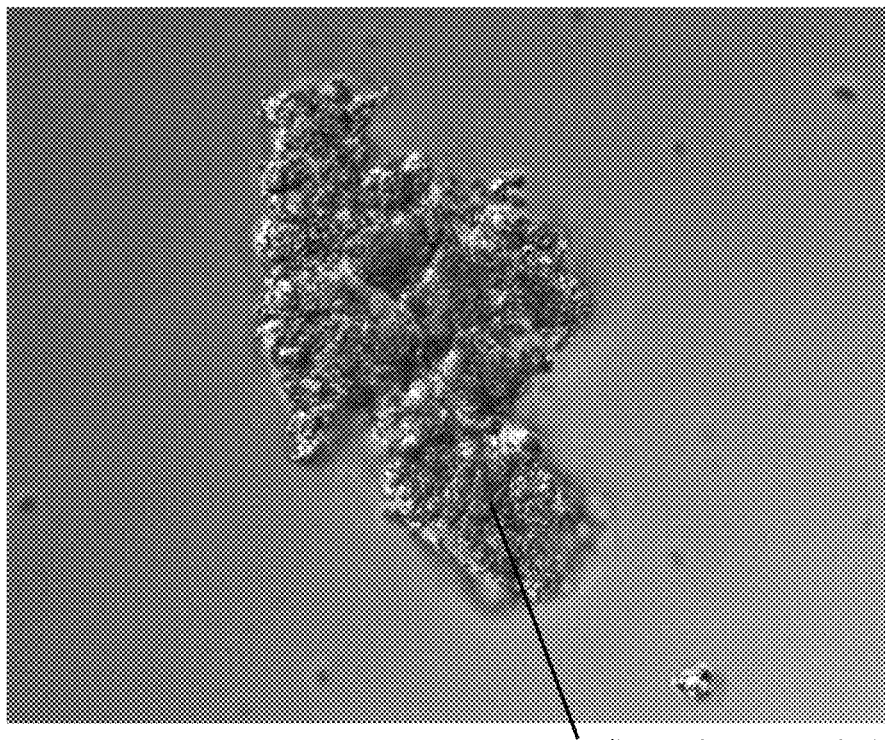
FIG. 6 Nanodiamond conjugated with an FITC mouse anti-monkey CD4 antibody Rhesus monkey lymphocyte being captured by antibody Nanodiamond with FITC mouse CD4 antimonkey antibody conjugated on the nanodiamond Rhesus monkey lymphocyte being captured by antibody Nanodiamond with FITC mouse CD4 antimonkey antibody conjugated on the nanodiamond Mouse anti monkey CD4 conjugated nanodiamond not attaching to a neutrophil Neutrophil Mouse anti monkey CD4 conjugated nanodiamond not attaching to a neutrophil Neutrophil

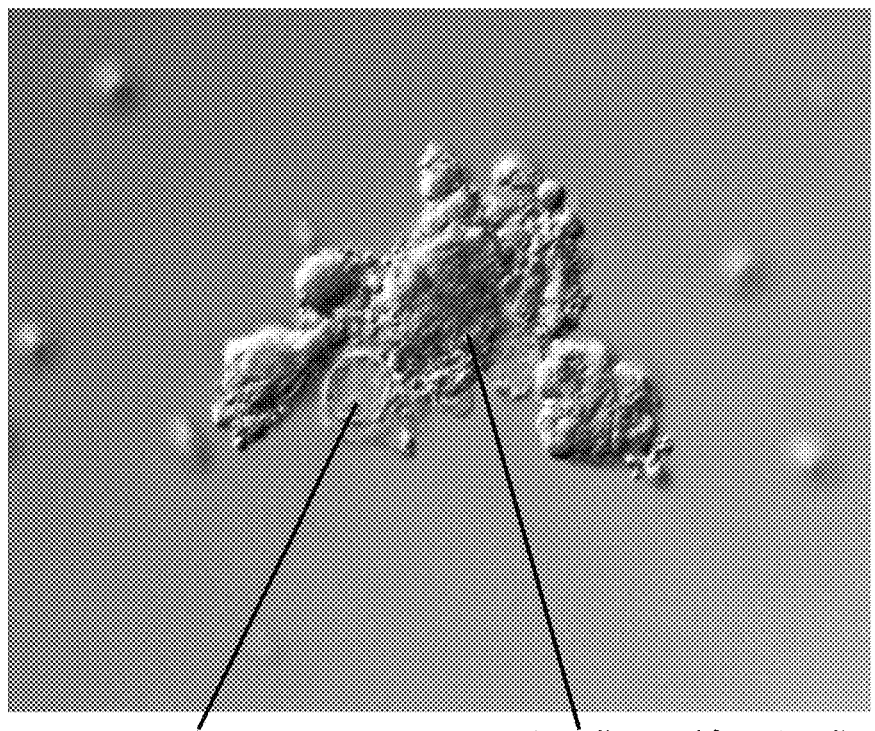
Captured monocyte    FIG. 11  Nanodiamond functionalized with a mouse CD14 antibody
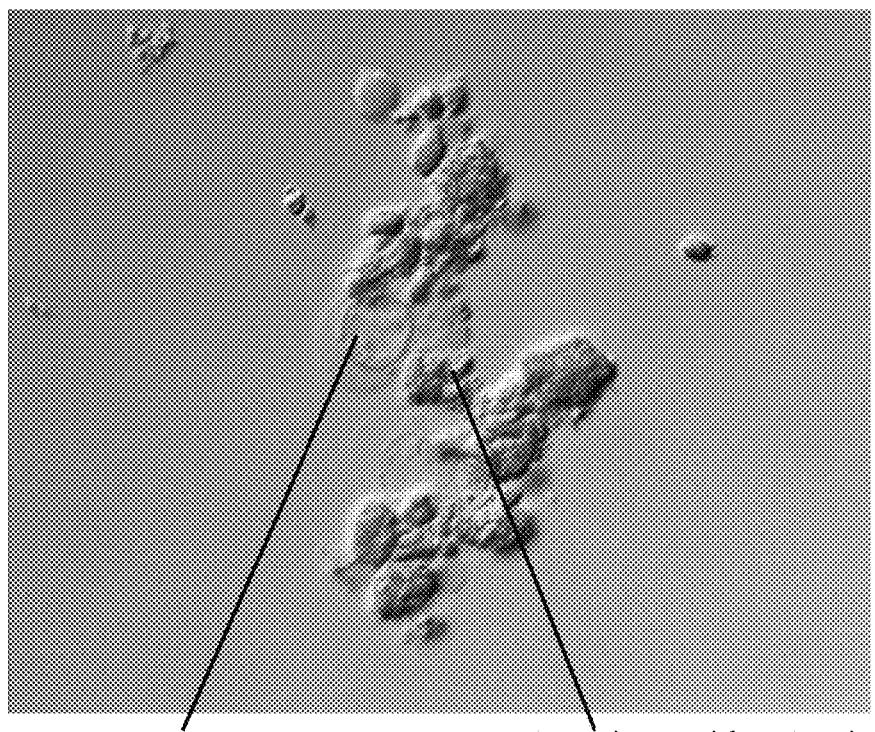
Captured monocyte    FIG. 12  Nanodiamond functionalized with a mouse CD14 antibody

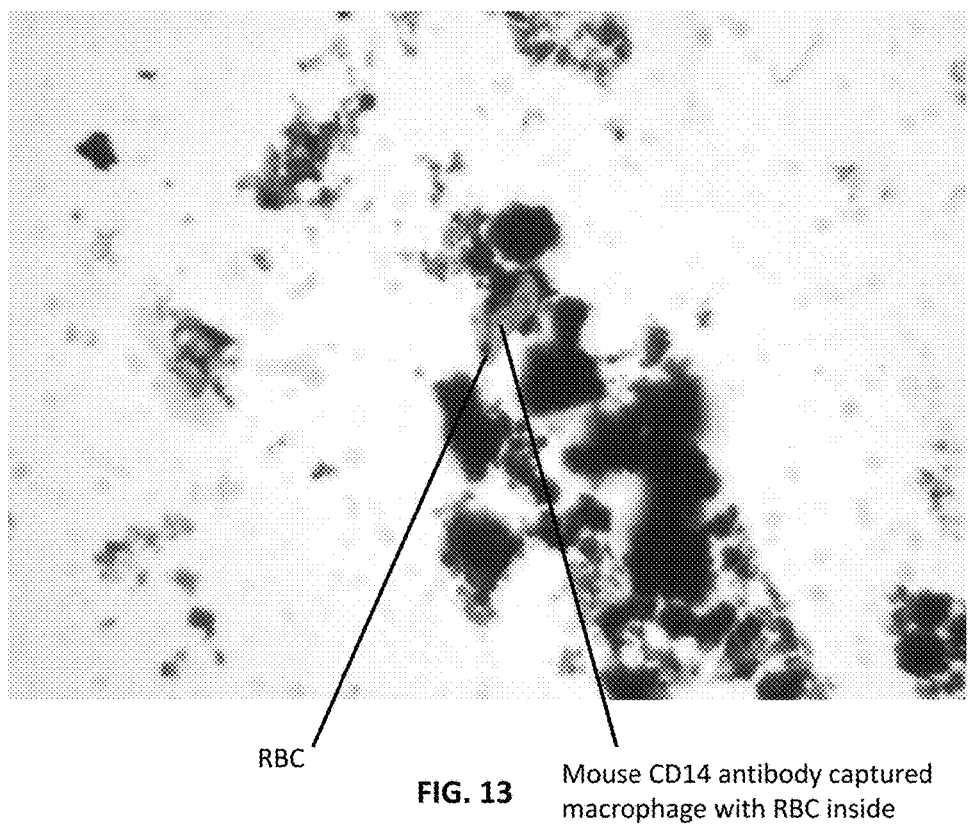
FIG. 13 RBC / Mouse CD14 antibody captured macrophage with RBC inside

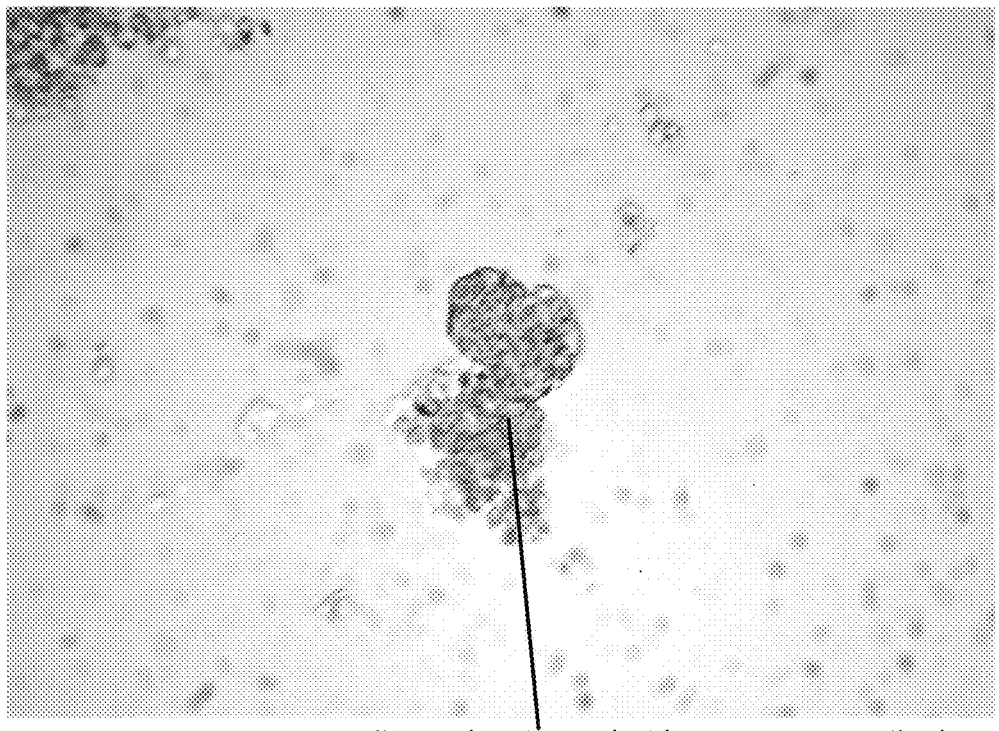
FIG. 14 — Nanodiamond conjugated with mouse CD14 antibody holding captured rhesus macrophages that have engulfed RBCs and are filled with rabbit opsonized sheep RBCs
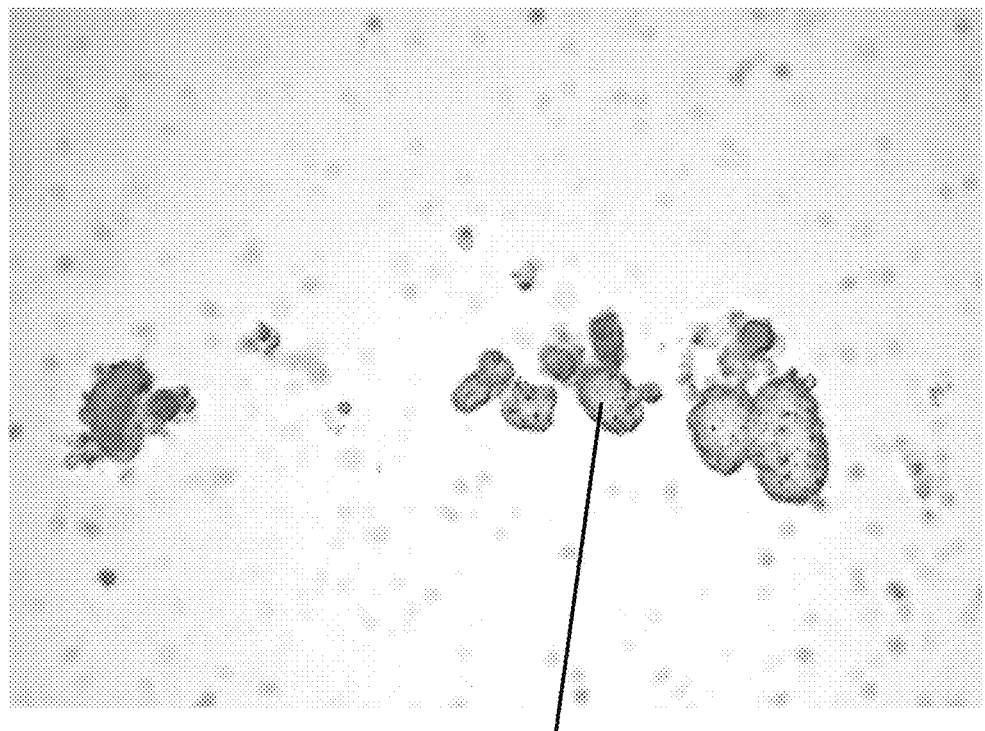
Nanodiamonds conjugated with mouse CD14 antibody holding captured rhesus macrophages that have engulfed RBCs and are filled with rabbit opsonized sheep RBCs
FIG. 15

REAL-TIME ADAPTIVE IMMUNE SYSTEM AND METHOD

CROSS REFERENCE TO RELATED APPLICATION(S)

This application claims the benefit of U.S. Provisional Application No. 61/433,859, filed Jan. 18, 2011, which is hereby incorporated by reference in its entirety for all purposes.

BACKGROUND OF THE INVENTION

A. Field of the Invention

The invention relates to systems and methods of using nanotechnology to synthetically replicate the body's immune function.

B. Description of the Related Art

Scientists have been studying the immune system and its components for many years to find ways to manipulate immune function for treatment of human and non-human patients. The need for the ability to control and manipulate the immune system has been increasing in view of the growing population trend of antimicrobial-resistant pathogens, an enlarging population of immuno-compromised individuals, and the elusive ability to effectively stimulate the immune system to counteract these invaders. The *Staphylococcus aureus* bacterium, for example, is well known for its ability to become multi-drug resistant, and it has emerged as a nosocomial threat to hospitalized patients with grave potential. The biologic spectrum of bacterial and viral resistance is growing and is not limited to the *Staphylococcus* species. The global threat of bioterrorism and the use of biological agents which have no vaccine or treatment are ever present and can exhibit profound, immediate mass effects on populations that are not currently prepared to respond on such an immediate and large scale.

Researchers have applied various methods to try to reproduce immune system functions or otherwise utilize immune system mechanisms to capture and/or analyze certain agents in the body. Plasmapheresis is one mechanism that allows for some immune system manipulation and control. The methodology includes removing blood from the patient, separating its components, removing a fraction of the removed blood, and returning a replacement fraction to the patient. The patient's affected blood products are removed and replaced with those of another healthy patient or with synthetics. Examples of diseases that have been treated using plasmapheresis include the following: Guillain-Barré syndrome Chronic inflammatory demyelinating polyneuropathy, Goodpasture's syndrome, Hyperviscosity syndromes, Cryoglobulinemia, Paraproteinemia, Waldenström macroglobulinemia, Myasthenia gravis, Thrombotic thrombocytopenic purpura (TTP), Wegener's granulomatosis, and Lambert-Eaton Syndrome (15). There are a number of benefits to rapid removal of auto antibodies and proteins in order to allow time for medications to arrest production of the antibodies and to take effect. However, there are a number of adverse effects with plasmapheresis, including transfusion reactions, risk of exposure to foreign blood products, clotting complications, and the need for the use of anticoagulants, such as citrates, that can cause hypocalcaemia. In addition, the blood must be separated out into its individual components, which complicates the methodology and requires specialized machinery.

Dialysis is another procedure involving a type of blood filtration. In dialysis, blood is removed from the patient, the blood is mixed with a dialysate to filter the blood of toxic waste products through diffusion of waste products, and the blood is returned to the patient. However, dialysis cannot be used to remove blood-borne bacteria, viruses, parasites, cells, cytokines, etc. from the bloodstream effectively for return to the patient in real time.

The ultimate goal of medicine is to treat the patient without causing harm. To date no methodologies have been developed that can remove targeted antigens or other unwanted agents from the body in real time without harming the patient. Further, there are no mechanisms for removing blood-borne bacteria, viruses, parasites, cells, cytokines, etc. from body fluids (e.g., the bloodstream) effectively so that clean fluid (e.g., blood) can be returned to the patient in real time.

SUMMARY OF THE INVENTION

The above-described problems and others are addressed by various apparatuses and methods described herein. The invention provides an external immune system using particles (e.g., nanodiamonds) to synthetically replicate the body's vital, innate immune functions. The invention can remove targets from a body fluid in real time without the need for conventional transfusion replacement, thus minimizing detriment to the patient. The invention can also present the particles or agents bound by the particles to the body fluid in real time. The invention removes targets, such as pathogens, viruses, bacteria, cytokines, proteins, cell lines, endotoxins, particulates, etc., for which an agent (e.g., an antibody) can be produced. The invention can also present a variety of targets to the body fluid. The invention replicates aspects of the immune system, providing the ability to monitor vital systems, providing a rapid diagnostic platform tool, providing the ability to "communicate" with the innate immune system through cell signaling and opsonization, providing the ability to "listen" to the immune system to identify activated, targeted components of the innate system, allowing cells to be presented to the body for use in antigen stimulation (modified vaccination), allowing cells to be targeted and removed from the blood stream, among numerous other functions. Through the creation and use of functionalized particles (that may or may not be complexed with agents) in a flow-through return system, the particle interactions allow for individualized treatment of blood-borne pathogens and disease spectra, and allow for rapid individualized diagnostics. The invention also provides a mechanism for defense against biological weapons of mass destruction. The invention can also sensitize the body towards recognition of a selected antigen without the antigen being introduced into the body proper, providing a modified form of "vaccination" through antigen presentation. The particle complexes can be uniquely and quickly disassembled and re-derived into its parts for reuse of the particle if required in less developed regions of the world.

The invention includes a number of different embodiments. In one embodiment, the invention is an external immune apparatus that comprises a container holding particles that have been functionalized to expose one or more binding sites for filtering of or presentation to a body fluid. The container is configured for receiving the body fluid through a first line (e.g., a delivery line), and the body fluid received passes through the container holding the particles. The binding sites of the particles, or one or more agents bound by the binding sites, can do one of at least two things. The binding sites/agents can bind targets in the body fluid for filtering out the targets from the body fluid as the body fluid passes across the particles to produce filtered body fluid that exits the container through a second line (e.g., a return line). The binding sites/agents can alternatively be presented to the body fluid for interaction with or modification of the body fluid as the body fluid passes across the particles to exit the container through a second line (e.g., a return line).

In another embodiment, the invention includes a method for filtering of or presentation to a body fluid. The method includes the steps of delivering the body fluid to a container through a first line (e.g., delivery line), the container holding a plurality of particles that have been functionalized to expose one or more binding sites. The method further includes performing one of at least the following two steps: 1) filtering, or causing to be filtered, the body fluid through the particles, wherein the binding sites of the particles or one or more agents bound by the binding sites bind targets in the body fluid for filtering out the targets from the body fluid as the body fluid passes across the particles to produce filtered body fluid, or 2) presenting, or causing to be presented, to the body fluid the binding sites of the particles or one or more agents bound by the binding sites for interaction with or modification of the body fluid as the body fluid passes across the particles. The method further includes the step of removing the body fluid from the container through a second line (e.g., return line). Some embodiments of the method include a step of inserting the container into or connecting the container to one or both of the first line and the second line. Some embodiments of the method also include the steps of detaching the container from one or both of the first line and the second line, replacing the particles in the container with new particles or replacing the container with a new container having new particles, and inserting the container with new particles or the new container into one or both of the first line and the second line. In addition, some embodiments include steps of identifying or evaluating the targets bound by the particles in the filtered body fluid as a diagnostic or analytic tool. Further, some embodiments include releasing one or more agents (e.g., therapeutic agents) bound by the particles into the body fluid as the body fluid passes across the particles.

In some embodiments of the above apparatus and method, the particles are nanodiamonds. In one embodiment, the container is attached to one of the first line and the second line, which are attached to a body for filtering the body fluid from the body in real time. In some embodiments, the body fluid is blood, and the first and second lines are intravenous lines attached to the body of a patient delivering blood to the container and for receiving filtered blood from the container. The container can be a removable cartridge that is insertable into or attachable to the first or second line. The binding sites exposed on the functionalized particles can directly bind the targets in the body fluid to produce the filtered body fluid. Alternatively, one or more agents (e.g., capture agents) bound by binding sites exposed on the functionalized particles can bind the targets in the body fluid to produce the filtered body fluid. In addition, the binding sites exposed on the functionalized particles can be directly presented to the body fluid as the body fluid passes across the particles. Alternatively, one or more agents bound by binding sites exposed on the functionalized particles can be presented to the body fluid as the body fluid passes across the particles. In this case, the agents presented to the body fluid can be exposed to the body fluid to provide vaccination or to produce an immune response in the body fluid.

The agents can be antibodies or antigens, or other agents. In one embodiment, the agents include a first agent that has captured a second agent, wherein the second agent captures the target(s) or wherein the second agent is presented to the body fluid. For example, the agents can include monocyte-differentiation antigens that have captured monocytes to convert the monocytes into macrophages, and wherein the targets are cells that are engulfed by the macrophages. In some embodiments, the agents comprise capture agents that have bound targets as capture agent-target complexes that are presented to or introduced into the body fluid. In some embodiments, the agents are antigen- or biomarker-tagged agents that enhance and target the immune system of the body for vaccination of or treatment of the body. In some embodiments, the agents are agents that function as T cells attached to signaling molecules or function as dendritic cells attached to signaling molecules. The agents and/or the targets can remain functional once bound by the particles. The targets can be selected from a group including, but not limited to, parasites, cytokines, antigens, antibodies, viruses, bacteria, pathogens, endotoxins, genetic material, cells, and a variety of other agents.

In another embodiment, the invention includes a method of functionalizing particles and conjugating the particles with agents. The method comprises the steps of placing the particles in an acid solution for a period of time to functionalize the surface of the particles to expose a plurality of binding sites on the particles and washing the particles in a solution that is less acidic than the acid solution until the particles reach a specified minimum pH. The method also includes adding agents to the particles with functionalized surfaces, wherein the exposed binding sites on the particles conjugate the agents. In some embodiments, the acid solution is 1N HCL and the period of time is at least 72 hours. In some embodiments, the washing further comprises washing the particles in a hypertonic saline solution, in a phosphate-buffered saline (PBS) solution, or in water. In other embodiments, the washing further comprises washing the particles in a hypertonic saline solution at least three times until the solution has a pH of about 5 to 6. The method can also further comprise a step of placing the particles in a hypertonic saline solution for a period of time following the washing of the particles. In this case, the method can then include a step of washing the particles in a phosphate-buffered saline (PBS) solution until the solution has reached a specified pH. In this embodiment, the washing of the particles in PBS can comprise washing the particles at least three times until the solution has reached a pH of about 6 to 7. In a further embodiment, the invention comprises a nanodiamond that is functionalized via the functionalization method described.

In still another embodiment, the invention comprises an analytic or diagnostic tool. The tool comprises a container holding a plurality of particles that have been functionalized to expose one or more binding sites. The container is configured to be placed into contact with a sample in a second container. All or a portion of the container holding the particles can be placed into contact with or submerged into the sample. The binding sites of the particles, or one or more agents bound by the binding sites, either bind targets in the sample or are presented to the sample for interaction with or modification of the sample. The particles or the sample are then analyzed (e.g., while the container is submerged or after removal of the container from the sample). The analysis can be done using a variety of methods, including using a separate diagnostic or other apparatus. The particles can be nanodiamonds or other particle types.

In a further embodiment, the invention comprises a method for using a container of particles as an analytic or diagnostic tool, wherein the particles have been functionalized to expose one or more binding sites. The method includes the step of placing the container into contact with a sample in a second container, wherein all or a portion of the container holding the particles can be placed into contact with or submerged into the sample. The method further includes the step of performing one of at least two steps. One of the steps is binding, or causing to be bound, targets in the sample by the binding sites or by one or more agents bound by the binding sites. The other of the steps is presenting, or causing to be presented, to the sample, for interaction with or modification of the sample, the binding sites or one or more agents bound by the binding sites. The method also includes the step of analyzing the particles or the sample following the performing of one of the steps (e.g., while the container is submerged or after removal of the container. The analysis can be done using a variety of methods, including using a separate diagnostic or other tool. The particles can be nanodiamonds or other particle types.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 is differential interference contrast (DIC) micrograph of a nanodiamond, according to an embodiment of the invention.

FIG. 2A illustrates an embodiment of the apparatus in which targets are removed from the body fluid. FIG. 2B illustrates an embodiment of the apparatus in which agents or targets are presented to the body fluid. FIG. 2C illustrates an embodiment of the apparatus in which the apparatus is used for diagnostics.

FIGS. 5 and 6 are micrographs of a nanodiamond conjugated with a fluorescein isothiocyanate-(FITC) tagged mouse anti-monkey CD4 antibody (FITC is the fluorescent tag to visualize the antibody on the nanodiamond), according to an embodiment of the invention. FIG. 5 is a DIC micrograph and FIG. 6 is a light micrograph, both taken using an Olympus BX61 microscope.

FIG. 7 is a light micrograph and FIG. 8 is a DIC micrograph, both taken using an Olympus VX61 microscope.

FIGS. 11 and 12 are light micrographs of a nanodiamond functionalized with a mouse anti-monkey CD14 antibody with a captured rhesus monkey monocyte, according to an embodiment of the invention.

FIG. 13 is a light micrograph of a mouse anti-monkey CD14-captured rhesus monkey macrophage with a rabbit opsonized sheep red blood cell (RBC) inside on a Wright stain slide (macrophage engulfed the RBC), according to an embodiment of the invention.

FIGS. 14 and 15 are light micrographs of nanodiamonds conjugated with mouse anti-monkey CD14 holding captured rhesus monkey macrophages that have engulfed and are filled with rabbit opsonized sheep RBCs, and the nanodiamonds also recognized the opsonization of the sheep RBCs and captured them as well, according to an embodiment of the invention.

DETAILED DESCRIPTION OF THE INVENTION

A. Definitions

Figure 2A:
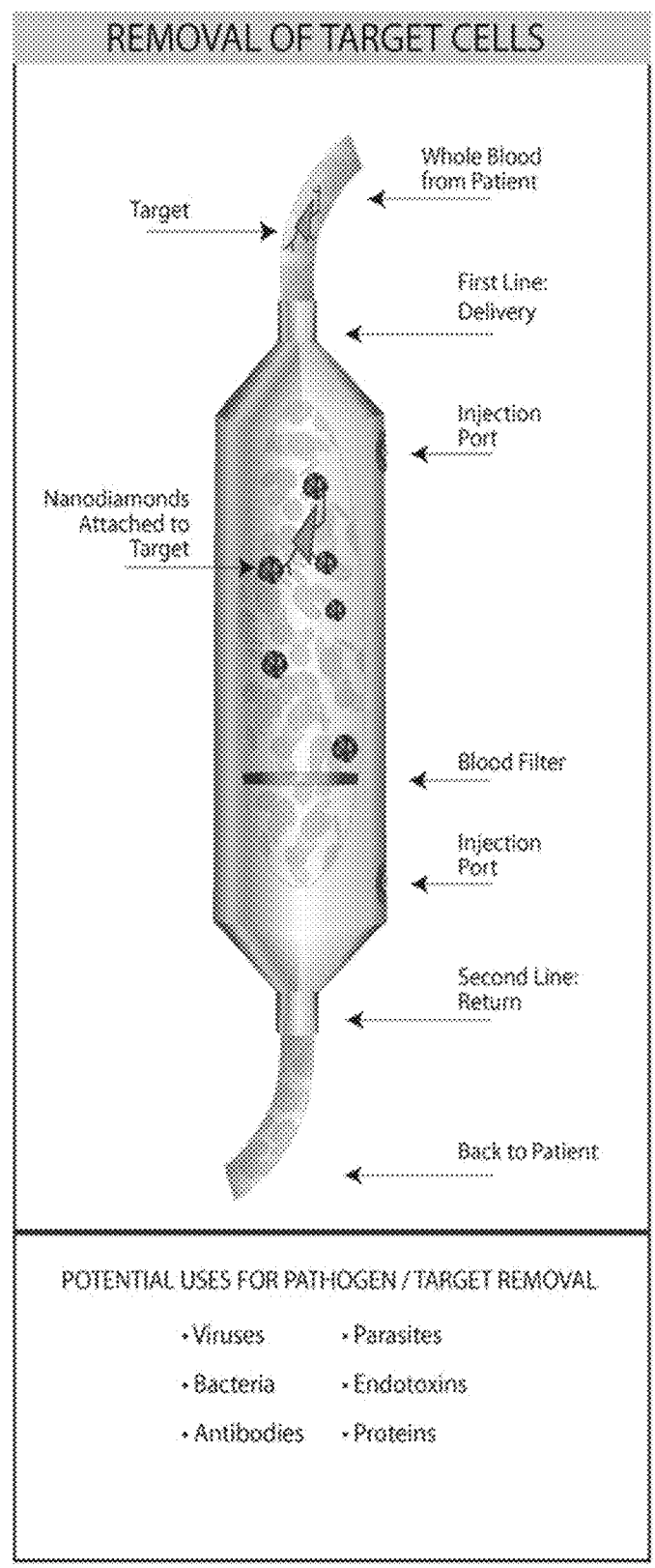
FIGS. 2A, 2B, and 2C are diagrams of the external immune apparatus, according to embodiments of the invention.

Terms used in the claims and specification are defined as set forth below unless otherwise specified.

The term "in vivo" refers to processes that occur in a living organism.

The term "in vitro" refers to processes that occur outside a living organism.

The term "mammal" includes both humans and non-human mammals, such as primates, canines, felines, murines, bovines, equines, porcines, among others.

The terms "particle" refers to particles used with the invention, including nanodiamonds, beads, microbeads, nanobeads, microparticles, nanoparticles, nanodiamonds, among others. The term "nanoparticle" includes nanodiamonds, nanobeads, among others.

The term "body fluid" refers to any type of bodily fluid found in mammals, such as whole blood or blood components, serum, digestive fluids, enzymes, bile, cerebrospinal fluid, peritoneal fluid, pleural fluid, sweat, tears, lymphatic fluid, among others.

The terms "body," "body fluid," "blood," and other terms referring to aspects of the body, body fluids, organs, etc. refer to the body, body fluid, or blood of a human patient or of any other mammal.

B. Particles/Nanodiamonds

The invention includes a number of aspects associated with particles, each of which will be discussed in more detail. Sizes of particles used with the invention (including nanodiamonds) typically range from 10 nm to 100 nm. However, other particle sizes, fractional sizes, or ranges could be used with the invention as well that fall within the 10 nm to 100 nm range (e.g., 20, 30, 35, 40, 50, 60, 65, 70, 80, or 90 nm) or fall outside of the 10 nm to 100 nm range (e.g., 5, 8, 105, or 110 nm). The invention can also include particles that are at least, at most, or fall between any of these sizes. The particle can be functionalized to expose one or more binding sites. The particle can be used in an external immune apparatus or method, in an analytic or diagnostic tool or method, among other uses. The invention also includes a method of functionalizing a particle, and conjugating it with one or more agents, along with a particle functionalized and conjugated via the method.

A variety of characteristics are desirable in particles used with the invention, including the following:

1) A particle that easily lends itself to antibody or antigen deposition and whose surfaces can be quickly and easily functionalized without toxic residues;
2) A particle that does not have toxic metabolites inherent in its qualities;
3) A particle that has biocompatibility;
4) A particle that is durable and will not dissolve in solution; and
5) A particle that has future ramp up capability for additional applications and methodologies.

In one aspect, the particle is a nanodiamond, which meets the above-listed standards. FIG. 1 illustrates a nanodiamond viewed using DIC microscopy. Diamond-based nanostructures, also known as nanodiamonds, have the physical properties expressed above but also incorporate ease in manufacture through several commercial processes. Nanodiamonds are unique in their characteristics of non-toxicity in a durable, lattice-based structure. Nanodiamonds generally carry hydrophilic —OH and —COOH groups which make them negatively charged, but the anionic charge does not affect the thermodynamic stability to any substantial degree (16, 17). When an electrical charge is placed on a nanodiamond, it does not hydrolyze water (22). This unique feature allows for development of in vivo electrical devices to measure biochemical processes for diagnostic application and pre-seizure identification with minimized or eliminated hydrolysis effects secondary to prolonged electrode contact. Drugs have been shown to easily incorporate with the surface of nanodiamonds utilizing simple sodium chloride (NaCl) protocols, and post-use disassociation accomplished through desalination (20). In studies previously conducted, it has been shown that, as particle size increases, so does the kinetic energy (17), making it desirable for column usage in immunoaffinity methodologies.

Nanodiamonds are durable and can withstand cleaning with boiling mixtures of sulfuric acid and perchloric acid without degradation (18). As with large size diamonds, nanodiamonds possess a high index of light refraction and light scattering. They also emit Raman signal which provides a fingerprint by which the molecules can be identified and detected within cells (18). This characteristic allows for utilization in DNA-based applications. The nanodiamonds can be produced by chemical vapor deposition for larger nanodiamonds, and nanodiamonds that are less than 10 nm can be produced through detonation techniques (19). The detonation technique was first synthesized in the 1980's by Los Alamitos Laboratories in the USA, after their discovery by the Soviet Union (19). Biocompatibility studies have been performed using detonation nanodiamonds (20, 21, 23). UV radiation for sterilization and dilution with deionized water has been used for cell culture cytotoxicity studies (21).

In tissue macrophage cultures, nanodiamonds have been shown to instantly attach to cell membranes and have a high affinity for proteins (20, 23). The nanodiamond's biocompatibility and physical transformations possible have been researched and manufactured in the form of thin-film coatings for use in hip, knee and organ implants such as the Jarvik heart. This process is accomplished through chemical vapor deposition (22). Carbon and secondary deposits maybe present from some suppliers using detonation-based production, so higher purity nanodiamonds are preferred. Nanodiamonds are also present in nature in the Arctic glaciers and in layers of geological sediment.

C. Agents and Targets

Various types of agents and targets can be used with the nanodiamonds or other particles of the invention. The term "nanodiamond/particle" is used throughout to refer to nanodiamonds or any other particles that might be used with the invention. In some embodiments, the functionalized nanodiamonds/particles are coated with or otherwise conjugated with or linked to one or more agents (e.g., antibodies or antigens) or other molecules of interest. In other embodiments, the functionalized nanodiamonds/particles are left uncoated. Agents can be capture agents that can capture targets to be removed from a body fluid or sample, or can be presentation agents that are presented to the body fluid for interaction with or modification of the body fluid or sample.

The particular agents and targets used can vary with different embodiments of the invention. In some embodiments, the agents are antibodies and the targets are antigens. In other embodiments, the agents are antigens and the targets are antibodies. In further embodiments, the agents are various different receptors (e.g., cell receptors) with target ligands. In still further embodiments, the agents are analyte-binding molecules with target analytes. In additional embodiments, the agents and/or targets can be proteins, parasites, cytokines, antigens, viruses, bacteria, pathogens, endotoxins, cells, cell lines, genetic material, DNA, RNA, oligonucleotides, oligoribonucleotides, antigen- or bio-marker-tagged agents that enhance and target the immune system, T cells attached to signaling molecules, dendritic cells attached to signaling molecules, etc. In further embodiments, the targets can be any target molecule for which an antibody is available or can be designed, or any protein. In some embodiments, the agent includes a first agent that has captured a second agent, and the second agent captures the target. For example, the agent can include antibodies with monocyte-differentiation antigens (e.g., CD14) that have captured monocytes, where the CD14 converts the monocytes into macrophages. In this case, the targets are cells (e.g., red blood cells) that are engulfed by the macrophages bound by the nanodiamonds/particles. In addition, the invention can be used in a variety of areas, such as protein expression profiling (e.g., cancer markers, cardiac markers, metabolic markers, cell signaling, chemokines, growth factors, endocrine, isotyping, matrix metalloproteinases, neurobiology, transcription factors/nuclear receptors, etc.), immunodiagnostics (e.g., allergy testing, autoimmune disease, HLA testing, infectious diseases, vaccine testing, newborn screening, etc.), biodefense/environmental, genomic research (e.g., microRNA assays or panels, gene expression profiling, genotyping, etc.), genetic diseases (e.g., cystic fibrosis, cytochrome p450, etc.), among other areas. Some of the various agents and targets are discussed in more detail below.

D. External Immune Apparatus and Analytic/Diagnostic Tool

Figure 2B:
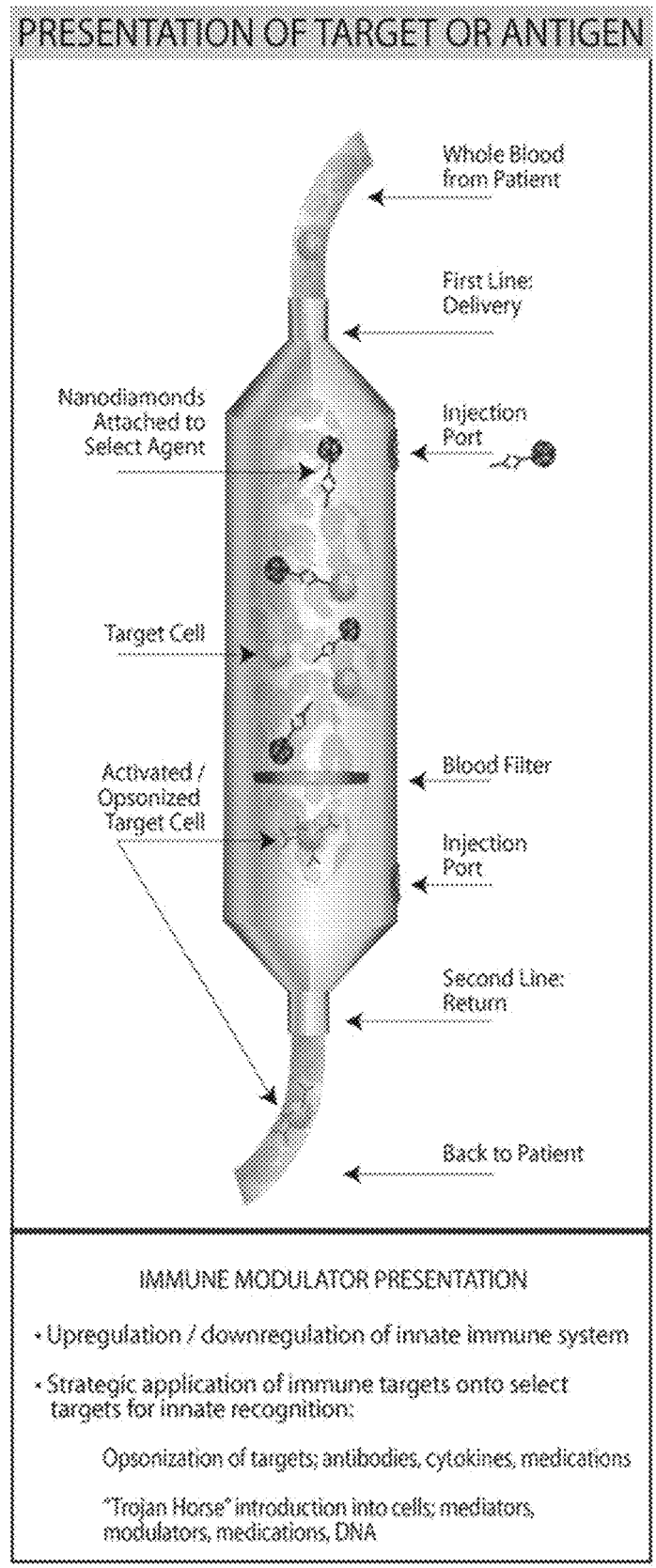
Figure 2C:
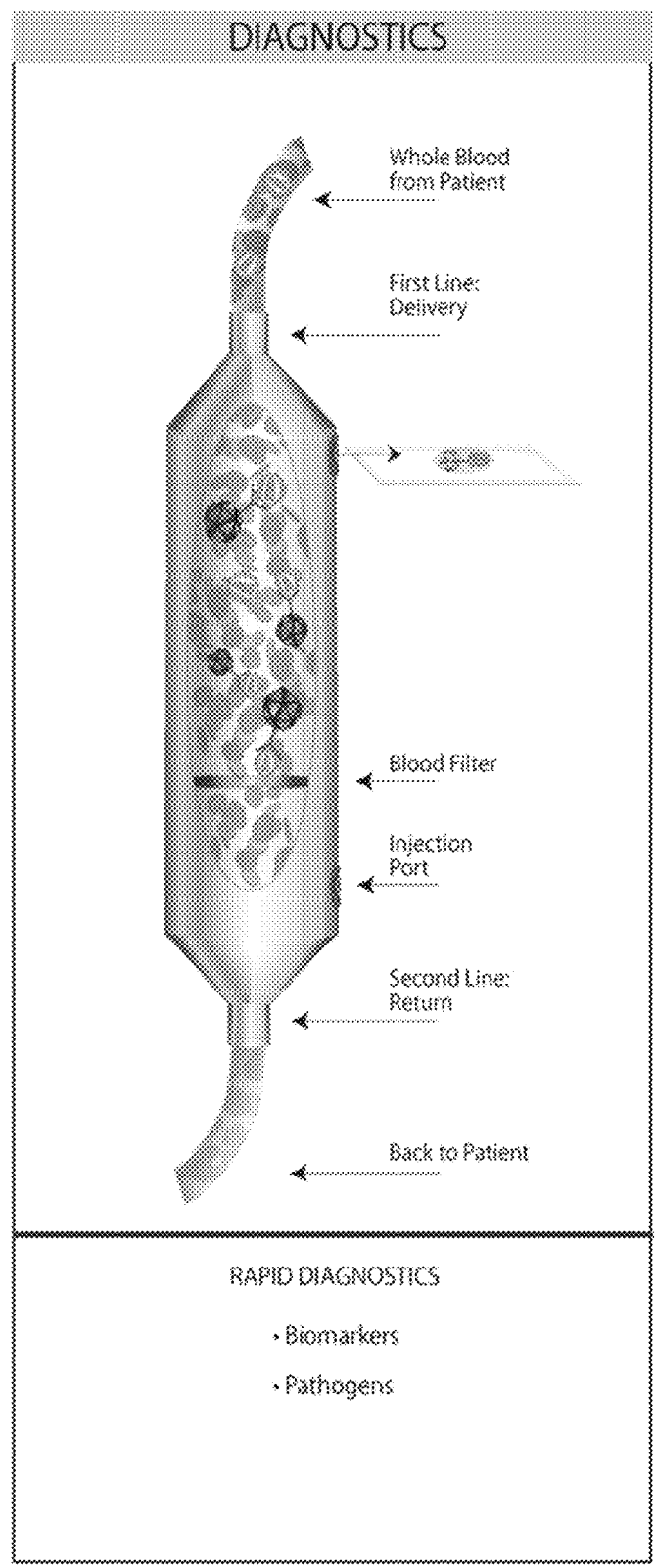

Referring now to FIGS. 2A, 2B, and 2C, there are shown embodiments of an external immune apparatus that comprises a container/cartridge holding nanodiamonds/particles that have been functionalized to expose one or more binding sites on the nanodiamonds/particles. The container is configured for receiving the body fluid (e.g., whole blood) through a first line (e.g., a delivery line). FIGS. 2A, 2B, and 2C illustrate embodiments where such a first/delivery line could connect to the device at the top of the container/cartridge. FIGS. 2A, 2B, and 2C further show that the body fluid passes through the container holding the nanodiamond/particles. The binding of targets in the body fluid can occur via two mechanisms. First, the binding sites on the nanodiamonds/particles can bind targets in the body fluid as it passes across the nanodiamonds/particles. Second, where one or more of the binding sites on the nanodiamonds/particles are linked to agents, the agents can bind targets in the body fluid as it passes across the nanodiamonds/particles. Similarly, the binding sites and/or agents bound by the binding sites can be presented to or otherwise placed into contact with the body fluid for interaction with or modification of the fluid. In other words, the apparatus can be a filtering apparatus for filtering out targets from body fluid (e.g., viruses, bacteria, antibodies, parasites, endotoxins, proteins, etc.), as shown in FIG. 2A. The apparatus can also be a presentation apparatus for presenting binding sites/agents/targets to the body fluid, as shown in FIG. 2B. The apparatus of FIG. 2B can be used for upregulation/downregulation of the innate immune system, for strategic application of immune targets/agents onto select targets/agents for recognition, including opsonization targets (e.g., antibodies, cytokines, medication, etc.), in a "Trojan Horse" introduction into cells (e.g., mediators, modulators, medications, DNA, etc.), and so forth. In addition, FIG. 2C illustrates the apparatus for use in diagnostics (e.g., biomarkers, pathogens, etc.).

In addition, one apparatus could have multiple functions, including two or all three of the functions shown in FIGS. 2A, 2B, and 2C. In some embodiments, the apparatus can include one or more injection ports, as shown in FIGS. 2A, 2B, and 2C. These ports can be used to inject materials into the container or to withdraw materials from the container (e.g., as show in FIG. 2C, in which materials have been withdrawn for analysis, etc.). The container is also configured for returning the body fluid (e.g., filtered fluid, or fluid that has been modified or interacted with by the nanodiamonds or agents) to the body through a second/return line. FIGS. 2A, 2B, and 2C illustrate where such a second/return line could connect to the device at the bottom of the container/cartridge.

The apparatus can be designed in various ways. In the FIGS. 2A, 2B, and 2C embodiments, the container or cartridge is a cylindrical device with non-reactive sides, though a variety of other designs and shapes are possible. In one embodiment, the apparatus has a diameter of 2 to 3 inches, though other sizes are also possible. The container/cartridge is filled with nanodiamonds (that may or may not be coated with agents) of the appropriate diameter for the targets (e.g., nanodiamonds greater than 40 microns, or less than 0.6 micrometers). In some embodiments, the container also includes one or more regular blood transfusion filters, as shown in FIGS. 2A, 2B, and 2C. In some embodiments, the container/cartridge is attached at the top to an IV blood line and has both a filtration device and intake region to increase turbulence if required. The bottom of the device can also be contiguous with a return filtration IV line to return blood or other body fluid to the body. In some embodiments, an intravenous bag is also connected to the lines. In additional embodiments, the container is a cartridge pre-loaded with nanodiamonds/particles. In some cases, the cartridge can easily be snapped into and out of the delivery/return lines. Thus, used cartridges can be easily removed and replaced with new, unused cartridges having fresh nanodiamonds/particles during treatment (or used particles can be replaced with new or fresh particles in a cartridge).

The container/cartridge can be connected to or separate from the body. For example, the nanodiamonds/particles or agents linked to the nanodiamonds/particles can be put into contact with body fluid in real time as it exits the body. In this case, the apparatus is connected to the body in some manner (e.g., via an IV line attached to the body). The nanodiamonds or agents can also be put into contact with body fluid that was extracted from the body (e.g., via intravenous withdrawal or other body fluid retrieval mechanism), and is separate from the body (e.g., in a container not linked to the body). The first and second lines can be used to provide the body fluid to the container, but the body fluid is not provided in real-time and the apparatus is not attached to the body in this case. Instead, the fluid can be first extracted from the body (e.g., intravenously or via other mechanisms), and then provided to and passed through the container, and then removed from the container. The body fluid may or may not be returned to the body intravenously or via other mechanisms. Thus, the filtering apparatus and/or presentation apparatus can be real-time or separate-from-the-body apparatuses. A single apparatus can be used for all of these designs, since the apparatus can be a container or cartridge that holds nanodiamonds/particles for use in a variety of applications, both real-time and separate from the body. However, different designs can be used for certain of the apparatuses, as well.

The external immune apparatus can be used for a variety of functions. For example, the apparatus can create immune complexes to clear a body fluid (e.g., the blood stream) of viral and bacterial component/cytokines, can create immune complexes to target cellular components (e.g., cancer), can focus the immune system on components of targets desired in real time, and so forth. In some embodiments, the apparatus uses antigen/antibody coated nanodiamonds that conjugate with whole blood and blood products in a free flowing gravity-based system to create immune complexes and filters to clear the blood stream of viruses, bacteria, cytokines, cells, etc. in real time and return the blood to the patient in a loop system. In another embodiment, the invention provides for real-time stimulation of the immune system. The apparatus can also provide the ability to substantially diminish a blood borne infection within a reasonable amount of time (e.g., less than 12 hours) without further debilitating the patient. The apparatus can further provide the ability to create human antibodies against a wide range of targets without the need for adjuvants and without the need for chimeric antibody production for use in vivo. The apparatus can also present cells to the body fluid for use in antigen stimulation, to provide a modified form of vaccination to the body.

As mentioned above, the apparatus can also be used in a "Trojan Horse" application that utilizes the fact the complexes (e.g., agent/target complex, etc.) can be removed from the surface of the nanodiamonds via changes in salinity. The now uncomplexed nanodiamonds can remain in the container, and the targets placed on the select pathogens, cells, etc. to form the complex can flow back into the body with the select tag (e.g., the agent now bound to the target). Further, two or more containers could be used in a sequence. The initial container can hold the nanodiamond complexed with an agent/target (i.e., an antibody, protein, cytokine, medication, etc.) to place onto a desired cell or other entity (i.e., a cancer cell, a virus-infected white blood cell, a pathogen, a protein, etc.) that has affinity for the desired cell/entity. Additionally, multiple agents/targets can be placed onto the cell/entity, either through the initial container or by utilizing a second container in sequence. The container can be flushed with a solution that provides a sufficient decease in salinity to release the complexes (e.g., agent/target bound to the cell/entity) from the nanodiamond. The salinity can be also be readjusted in a downstream line prior to reaching patient, if desired. The nanodiamond itself can remain in the cartridge, and now the desired cell/entity has been tagged or opsonized with the agent/target. The cell/entity carrying this agent/target returns to the blood stream with the agents/targets on the surface for providing further interaction in the body. For example, this can occur through ingestion of the cell/entity by macrophages where specific cytokines are the agents/targets, through antigenic presentation of the desired cell/entity to the immune system that may have previously not recognized the cell/entity as one to be destroyed (though it is now recognized due to the presence of the agent/target), through release of medication if ingested by virus-infected cell specifically opsonized for ingestion, and so forth.

Another aspect of the invention is an analytic or diagnostic tool comprising a container holding functionalized nanodiamonds/particles and a method of using such a tool. The container is configured to be placed into contact with a sample in a second container. The sample can contain any materials, targets, target molecules, etc. which are to be analyzed. All or a portion of the container holding the nanodiamonds/particles is submerged into the sample. Thus, in this embodiment, the cartridge can be a cartridge that is dipped into or allowed to sit for a period of time in a sample. The binding sites of the particles, or agents bound by the binding sites, can bind targets in the sample or can be presented to the sample for interaction with the sample or modification of the sample. The particles and/or the sample can then be analyzed. As one example, specific agents can be complexed with the nanodiamonds/particles, so targets can be identified and entrapped by the complex allowing for identification of the presence of the target quickly and efficiently. Further, phagocytic cells (e.g., macrophages) can be attached to the particles and can selectively engulf their targets for use as diagnostic identifiers of cells and molecules that may be recognized by a phagocytic cell. While these may not visualized directly through traditional bench top means due to their sizes, this tool makes their selective capture possible.

E. Methods/Uses of the Invention

The invention further includes various methods of use. In one embodiment, the invention includes a method for filtering of, or presentation to, a body fluid. The method includes the steps of delivering the body fluid to a container holding nanodiamonds/particles through a first line. The method also includes filtering (or causing to be filtered) the body fluid through the nanodiamonds/particles, or presenting (or causing to be presented) to the body fluid the binding sites (or agents attached to the binding sites) of the nanodiamonds/particles. The method also includes removing the body fluid (e.g., filtered or modified body fluid) from the container through a second line. The method can also include inserting the container into one or both of the lines, and can include detaching the container and replacing it or the particles in it with a new container/new particles, and then re-inserting the container into the line(s). The method can further include exposing the body fluid to agents bound by the nanodiamonds/particles to provide vaccination or to produce an immune response, or releasing agents (e.g., therapeutic agents) bound by the particles into the body fluid. The method can also include identifying or evaluating the targets bound by the particles in the body fluid as a diagnostic tool. Similar to the apparatus, there can be methods performed in real-time or performed separate from the body. In some embodiments, this method is used with the apparatus described above. However, this method can be performed with other apparatus designs, as well. In addition, the methods include using a container or cartridge as an analytic or diagnostic tool, as described above.

The container/cartridge of the invention can be used in a wide array of areas. In one embodiment, the invention can be used in harnessing or removing cytokines Several cytokines have been shown to be released during acute life-threatening endotoxic and shock related events. These include tumor necrosis factor alpha (TNF-alpha), an inflammatory cytokine that is the precursor to multiple organ failure in a myriad of disease states (13), IL-6 (interleukin-6), a marker of acute inflammation, and endotoxins from the causative agents themselves (13, 14). Antibodies have been developed to identify and isolate these cytokines, but their removal from the affected body in mass quantities has remained elusive. In addition, infected cells produce antigens on their cell surfaces, and the antigens express their own individual cell surface antigen markers, as well. The invention uses the antigen cell surface markers and uses antibodies in a manner that does not cause deleterious effects to the body. The invention can remove cytokines, antigens, viral and bacterial particles, cells, etc. from the living body in real time or separate from the body. For example, cytokines produced during acute events (e.g., life-threatening endotoxic and shock-related events) can be removed from the body in real time to treat the body during such life-threatening, acute events.

Antigen-antibody interactions can occur within direct contact time +/−53 seconds (16). The dependent factor is the affinity of the antibody being used, which determines whether the bond remains strong and adherent or is broken. Strong affinity antibodies are optimal for usage with the invention. The process of immunoaffinity chromatography takes advantage of these antibody/antigen interactions. The process is reversible and the complexes can be released through strong changes in pH (e.g., pH 4.0 and below). The nanodiamonds/particles can be washed of their antibodies and/or antigens and re-complexed for future use if required without strong pH changes which can be deleterious to living systems. The ability to remove antigen-antibody complexes quickly and easily allows for the use of complex "triads." In this case, the nanodiamond/particle plus agent complexes attach to a target forming a triad. These can be used for identification of cell types or markers present (e.g., cancer identification, such as identification of clear margins by the surgeon in surgical cancer removal) and this can be followed by un-complexing and removal of the nanodiamond itself, leaving behind an antigen-tagged target (e.g., opsonization of a target molecule) for the innate immune system to hone in on, thereby enhancing and targeting the innate immune system to remove unwanted cell lines or biomarkers if desired (e.g., an "attack here" marker for the body). The nanodiamonds/particles can also be reused, if desired. The nanodiamonds can be autoclaved if needed to manage blood-borne safety due to individual homodynamic passage (23).

Because the apparatus involves extracorporeal blood flow, it is possible that anticoagulants may be used (e.g., heparin-protamine, prostacyclin, citrate) to prevent thrombosis in the first and second lines. If lipid-based anticoagulants are used (though this is not required by the invention), these can be removed through the apparatus described herein, which can include, for example, a separate cartridge with nanodiamonds having antibodies tagged to the anticoagulant before returning to the patient. This minimizes the amount of anticoagulant burden the body carries secondary to the procedure to minimal levels. In addition, use of anticoagulants can be avoided via a fast flow mechanism, or low doses of heparin could be used.

In the case of targeted cell removal, the complexes attach to a cell target while at the same time leaving untargeted cells un-complexed, which allows for removal of particular cellular targets. Also, by having the ability to bind a large, particle-like cell, the complex can present a targeted cell with desired markers to present to the immune system for activation of the immunostimulatory cascade in a form of modified vaccination. The complex can also be designed to function as a "T" presenter cell or a dendritic cell. The complex is thus used to convey activation signals to the body against specific targets dependent upon the signaling molecules that are attached. The invention can further be used in cancer therapies, molecular, bacterial, anti-parasitic vaccinations, and presentations to the body for enhanced immunostimulatory effect.

Currently human antibodies are produced through the use of various methods using animal, viral and bacterial species which can lead to rejection and inflammatory conditions secondary to the foreign proteins. This has created a void of purely human antibody production. The invention can be used in the acute stages of viremia in which the pathogens are blood borne or in the chronic stages of blood-borne bacterial infections in which the body is overwhelmed with antigens and cytokines. The invention can also remove target antigens that can be created using the invention and then used to clear the blood or other body fluids of target molecules. The invention can further be used to create human antibody targets. Thus, the invention can be used during an acute viral attack or infection to clear the blood of the viral particles or other unwanted agents to reduce viral or bacterial load or attempt to gain control.

F. Functionalizing and Conjugating Nanodiamonds/Particles

Another aspect of the invention is a method of functionalizing the nanodiamonds/particles and conjugating agents to the nanodiamonds/particles. The method includes the steps of placing the nanodiamonds/particles in an acid solution for a period of time to functionalize the surface of the particles to expose a plurality of binding sites on the particles. In one embodiment, the nanodiamonds/particles are placed in 1N HCL for at least 72 hours, though other acid solutions can also be used, and different amounts of time can be used (e.g., 24 hours, 36, hours, 48 hours, 5 days, 1 week, etc.). The method also includes washing the nanodiamonds/particles in a solution (e.g., hypertonic saline solution, phosphate-buffered saline (PBS) solution, or water) that is less acidic than the acid solution until the particles reach a specified minimum pH. In one embodiment, where the nanodiamonds/particles are washed in a hypertonic saline solution, they can be washed at least three times until the solution has a pH of about 5 to 6, though other variations are also possible (e.g., washing once, two times, four times, etc., to a pH of 4, 7, 8, etc.). In some embodiments, the nanodiamonds/particles are then placed in a hypertonic saline solution for a period of time following the washing of the particles. In some embodiments, following the placing of the particles in the hypertonic saline solution, the method includes a step of washing the particles in PBS until the solution has reached a specified pH (e.g., washing at least three times until the solution has reached a pH of 6 to 7, though other variations are also possible). These steps prepare the nanodiamonds/particles for conjugation of one or more agents to the nanodiamonds/particles (or to the binding sites made available via the functionalization). The method further includes adding agents to the particles with functionalized surfaces, wherein the exposed binding sites on the particles are conjugated with the agents.

In addition to the method of functionalizing/conjugating, the invention also includes a nanodiamond functionalized via this method. The nanodiamond can also be conjugated with an agent of interest via this method.

G. Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. Each of the examples below can be performed with nanodiamonds or other particles in a container/cartridge, such as that described above. These can be performed with the container/cartridge in a real-time external immune apparatus, in a separate-from-the-body immune apparatus, or in an analytic or diagnostic tool. The examples below provide particular ways of using or applying the invention, though any of the other methods or method steps described in this application can also be used.

a. Example 1: Quality Control, Functionalization/Conjugation of Nanodiamonds/Particles, and Capture of Targets Quality Control for Nanodiamonds/Particles and Functionalization Specifications of nanodiamonds that were quality controlled/verified are:
1 gram 50 nm single crystal detonation nanodiamond with average particle size 50 nm (SYN-50), incombustible impurities content 0.5%, zeta potential −40 mV, water based slurry with 1 wt % of ND A second sample of 1 gram of the tight aggregate 85 nm to 100 nm negative zeta potential detonation nanodiamond with incombustible impurities content 0.5%, zeta potential −40 mV, water based slurry with 1 wt % of ND.

Steps performed include the following:
1) Mild agitation (100 W VWR 150D sonicator) performed for 30 seconds to disperse the single crystal sample.
2) Filtered through a BD Falcon® 35 μm snap cap cell sorter filter to remove any extremely small particles. Particles required for the study varied in size. Determined largest filter size that can be used to entrap the nanodiamonds.
3) Allowed particles to sit in 1N HCL for 72 hours to remove any incombustible impurities and functionalize surface (measured PH 1-2 via litmus paper).
4) After 72 hours, washed particles with either hypertonic saline or DNA free water to a minimum PH of 5-6, centrifuge at 15,000 rpm between washes. Approximately 3 washes were used to reach PH 5-6 in small volume.

5) Particle measurement and quantification that was used:
  a. Raman Spectroscopy
  b. FTIR (Fourier Transform Infrared) Spectroscopy—micro Raman 514.5 nm laser
  c. TEM (Transmission Electron Microscopy)—photograph using gold grid (do not use copper grid)
  d. Flow cytometry
  e. Possible Luminex if unable to obtain particle count with other measures
  f. Fluorescent microscopy—Olympus BX61 red channel Nanodiamond/Particle Conjugation
Steps performed include:
1) Conjugated nanodiamond with antibody using hypersalinity
  a. Added 5 μl nanodiamonds to 20 μl of 7.2% hypertonic NACL solution
  b. Visually removed hypertonic saline
  c. Added 5 μl antibodies
  d. Gently mixed (rock) for 2-5 minutes
  e. 40× polarized lens light microscopy visualization/verification of particle presence through innate fluorescence with UV verification of FITC antibody presence
  f. Conjugation using above methodology with PBS. Started particle in hypertonic saline to functionalize, performed three rinses in PBS PH check=6-7, and began antibody conjugation. Results: conjugation was noted with target macrophage and opsonized RBC's.

Quality Control for Conjugation
Steps performed include the following:
1. Quality control to determine if antibody on nanodiamond particle attached and affixed in the proper position to acquire a target. Note that extreme desalination should cause release of antibody. If no conjugates found, consider and check the tonicity of the solution. Reverse osmosis water caused enough of a desalination shift to unconjugate antibody from the particle observed via electron microscopy during proof of concept when hypertonic saline used to conjugate.

Capture of Targets by Conjugated Agent and Verification of Capture
Steps performed include the following:
1) Determined if antibody is functional
  a. Placed 1 aliquot of conjugated particle/antibody with equal aliquot of antigen target. It was found during proof of concept ratio did not have to be 50/50. Differing ratios appeared to be effective, dependent upon contact possibility in total volume created.
  b. Verified complexes via electron microscopy, light microscopy for cell capture and fluorescent microscopy for FITC and verification of nanodiamond particle using natural fluorescent signature.
  c. Verified ability of captured cell to function completed with direct visualization of captured macrophage engulfing target RBC while captured by nanodiamond particle, presence of hemosiderin particles in captured macrophages after 12 hour exposure to target RBC while captured by nanodiamond particle at 37 degrees centigrade. Light microscope used for visualization and photography of the above.
  d. Verified ability to stain complexes without loss of complex on slide—Wright's stain placed on air dried slide of complex with macrophage and target RBC's. Nanodiamond particles showed uptake of stain as well. Buffer time was decreased from 5 minutes to 3 minutes for most effective staining for viewing slide. No appreciable loss of particles and complexes were noted.

b. Example 2: Goat Anti-Rabbit Antibody Conjugation

Figure 3:
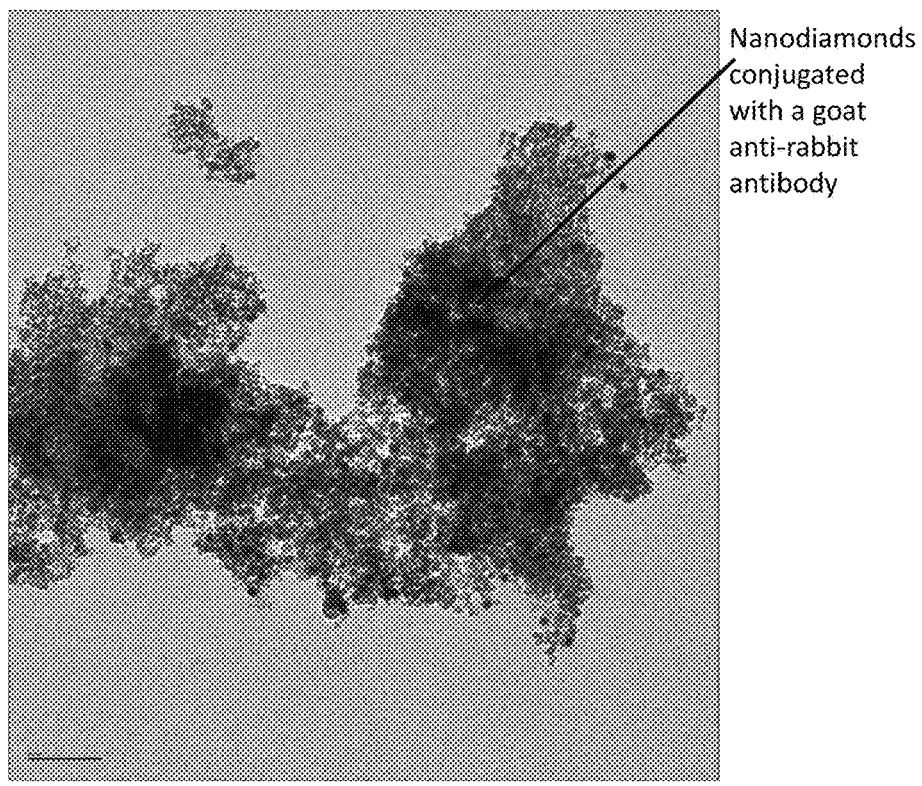
FIG. 3 is a transmission electron micrograph of nanodiamonds conjugated with a goat anti-rabbit antibody having a gold tag (dark black spots are the gold tags for visualization of the antibody on the nanodiamond), according to an embodiment of the invention.
Figure 4:
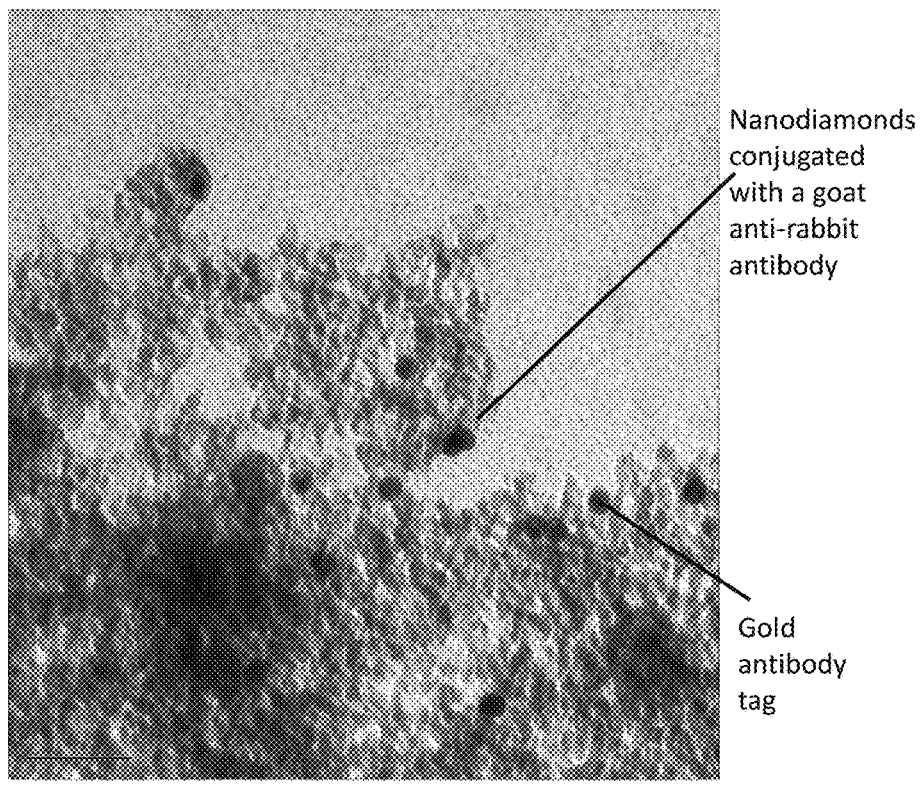
FIG. 4 is a transmission electron micrograph of a gold antibody tag, according to an embodiment of the invention.

FIG. 3 illustrates an example of the conjugation of nanodiamonds with antibodies that was performed. The quality control, functionalization, and conjugations steps described above were performed for this Example, as well as for the Examples below (unless otherwise noted). FIG. 3 is a micrograph of nanodiamonds conjugated with goat anti-rabbit antibodies. In other words, it is a goat antibody that has an antigen-binding site for binding rabbit antigens. Thus, this goat anti-rabbit antibody will capture goat antigens and targets expressing rabbit antigens. The goat anti-rabbit antibody has a gold tag that allows for visualization of the nanodiamond conjugated with the antibody. The gold tags are the dark black spots in the micrograph. FIG. 4 is a micrograph showing the gold antibody tag. The gold tag was obtained from Ted Pella, Inc. The supplier was BBInternational. The catalogue number for the ¼ ml amount of 10 nm gold was 15726.

c. Example 3: Mouse Anti-Monkey CD4 Antibody Conjugation

FIGS. 5 and 6 illustrate another example of conjugation of nanodiamonds with antibodies that was performed. FIGS. 5 and 6 are micrographs of the nanodiamond conjugated with a fluorescein isothiocyanate (FITC) mouse anti-monkey CD4 antibody. In other words, FIGS. 5 and 6 illustrate a nanodiamond that has bound a mouse antibody that is has an antigen-binding site for binding monkey antigens. Thus, this mouse anti-monkey antibody will capture monkey antigens and targets expressing monkey antigens. The antibody is also a CD4 (cluster of differentiation 4) antibody. CD4 is a glycoprotein expressed on the surface of T-helper cells, monocytes, regulatory T cells, macrophages, and dendritic cells. As a co-receptor, CD4 assists the T cell receptor in activating its T cell following an interaction with an antigen-presenting cell. FITC is the fluorescent tag used to visualize the antibody on the nanodiamond.

d. Example 4: Mouse Anti-Monkey CD4 Antibody Capture of Monkey Lymphocyte

Figure 7:
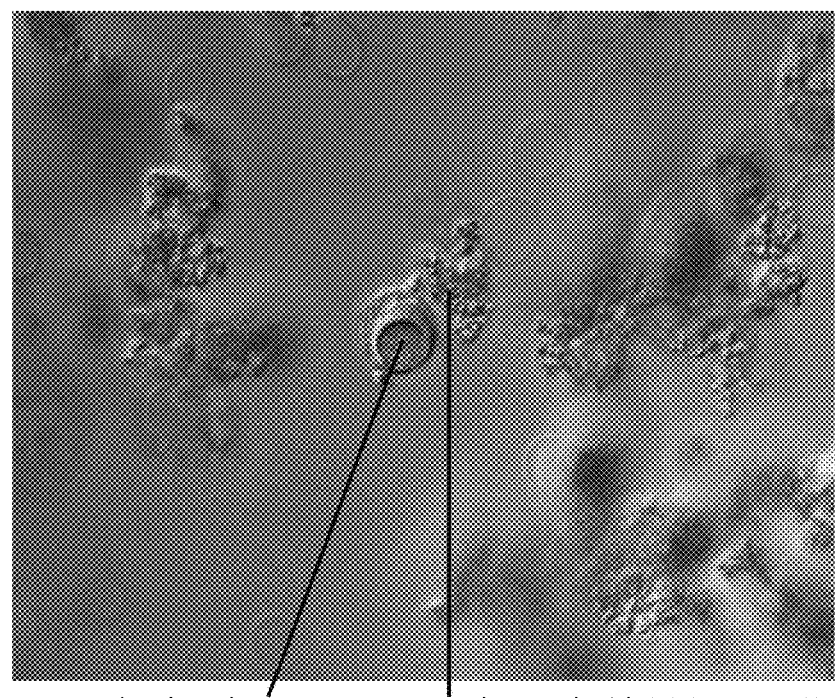
FIGS. 7 and 8 are micrographs of a nanodiamond with FITC mouse anti-monkey CD4 antibody conjugated with the nanodiamond capturing a rhesus monkey lymphocyte, according to an embodiment of the invention.
Figure 8:
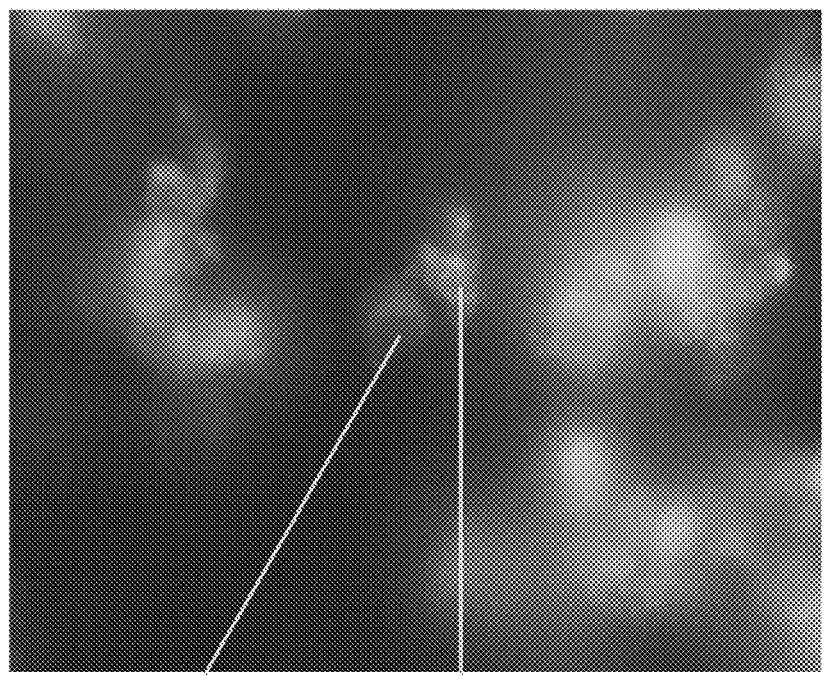
Figure 9:
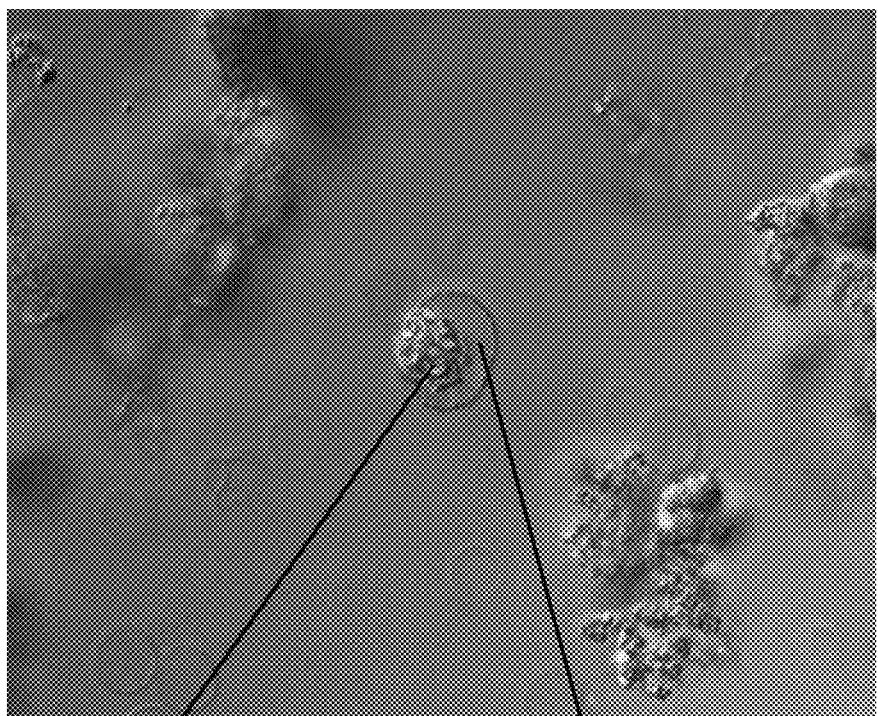
FIGS. 9 and 10 are light micrographs of a mouse anti-monkey CD4 conjugated particle being selective in its binding capacity and not capturing a neutrophil (i.e., since CD4 is for lymphocytes of the T-cell class, macrophages, and monocytes, it generally should not conjugate with neutrophils), according to an embodiment of the invention.
Figure 10:
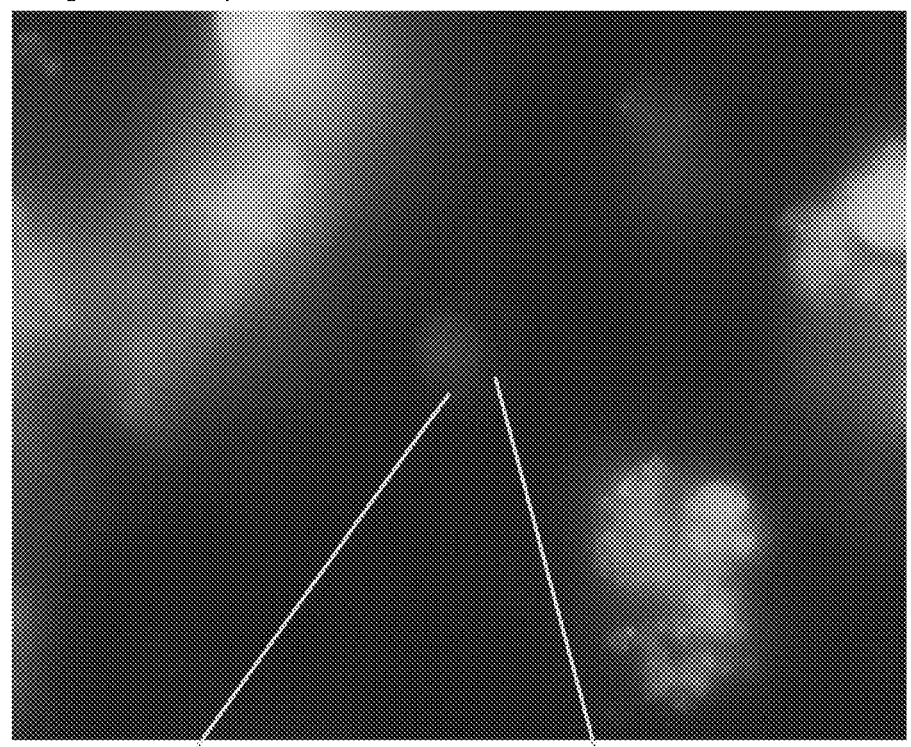

FIGS. 7 and 8 illustrate capture of targets by the agents that was performed. Verification of capture of the target by the antibody described above was performed for this Example as well as for the Examples below (unless otherwise noted). FIGS. 7 and 8 are micrographs of the nanodiamond with FITC mouse CD4 anti-monkey antibody conjugated on the nanodiamond (as was shown in FIGS. 5 and 6), but here the antibody is capturing a rhesus monkey lymphocyte. Since the mouse antibody is an anti-monkey antibody, it will bind cells expressing monkey antigens, such as a monkey lymphocyte. Lymphocytes are a type of white blood cell in the immune system of vertebrates. Examples of lymphocytes include T cells, B cells, and natural killer cells. The mouse CD4 anti-monkey antibody is fluorescently tagged with FITC for visualization of the antibody-nanodiamond complex. FIGS. 9 and 10 are micrographs of the mouse CD4 anti-monkey antibody conjugated particle being selective in its conjugation and not attaching a neutrophil (i.e., since CD4 is for lymphocytes of the T-cell class, macrophages, and monocytes, so it generally should not conjugate with neutrophils).

e. Example 5: Mouse Anti-Monkey CD14 Antibody Capture of Rhesus Monkey Monocyte FIGS. 11 and 12 illustrate an example of capture of targets by the agents that was performed. FIGS. 11 and 12 are micrographs of a nanodiamond functionalized with a mouse anti-monkey CD14 antibody (anti-CD14 molecule) that has captured a monocyte. CD14 (cluster of differentiation 14) is a surface antigen encoded by the CD14 gene, and is a component of the immune system. CD14 is primarily expressed by monocytes/macrophages. Cells expressing the CD14 protein are monocytes that can differentiate into various other cells, such as macrophages and dendritic cells (where differentiation is encouraged by cytokines, such as interleukin-4 (IL-4)). Thus, the CD14 antibody of FIGS. 11 and 12 has captured a monocyte, which expresses CD14.

f. Example 6: Mouse Anti-Monkey CD14 Antibody Capture of Rhesus Monkey Macrophage, which Engulfed a Red Blood Cell FIG. 13 illustrates an example of the capture by agents of targets converted into agents that capture targets themselves. As explained above, CD14 converts monocytes into macrophages. The CD14 acts with other proteins to mediate the immune response of monocyte/macrophages to bacteria as well as other foreign antigens that have invaded the body. Rhesus monkey monocytes were stimulated in culture with sheep red blood cells to become macrophages. A mouse anti-monkey CD14 antibody (anti-CD14 molecule) is placed on the particles that then recognized the CD14 on the macrophages and bound them to the particle. FIG. 13 is a micrograph showing the CD14-captured macrophage, and the macrophage on the particle then engulfed a rabbit opsonized sheep RBC. Antibody opsonization is the process by which a pathogen is marked for ingestion and destruction by a phagocyte. Opsonization involves the binding of an opsonin, i.e., an antibody, to a receptor on the pathogen's cell membrane. After opsonin binds to the membrane, phagocytes (e.g., monocytes or macrophages) are attracted to the pathogen. Thus, in this experiment, sheep RBCs are opsonized or bound to rabbit antibodies, and so the rhesus monkey macrophage recognizes and becomes attracted to the rabbit antibodies on the sheep RBC, resulting in the sheep RBCs being engulfed by the macrophage. FIG. 13 shows the RBC inside the macrophage on a Wright stain slide.

g. Example 7: Mouse Anti-Monkey CD14 Antibody Capture of Rhesus Macrophage that has Engulfed a Rabbit Opsonized Sheep Red Blood Cell FIGS. 14 and 15 illustrate another example of the capture by agents of targets that are converted into agents and capture targets themselves. FIGS. 14 and 15 are micrographs of the nanodiamonds conjugated with mouse anti-monkey CD14 antibody holding captured rhesus monkey macrophages that have engulfed rabbit opsonized sheep RBCs. The rhesus monkey macrophage recognizes and becomes attracted to the rabbit antibodies on the sheep RBC, resulting in the sheep RBCs being engulfed by the macrophage. However, in addition to that, the nanodiamonds also recognized the opsonization of the sheep RBCs themselves (i.e., sheep antibodies on the sheep RBCs) and captured them as well because of their antibody presentation.

Thus, the nanodiamonds will capture a selected target regardless of species. Further, a captured cell line is still functional while captured and can possibly be controlled. The particles can capture cell lines and present them for synthetic vaccination/secretion of select antibodies, proteins, cytokines, etc. The nanodiamonds can further selectively capture cells and use a targeted, presented antibody on the nanodiamonds for diagnostic purposes, etc. In addition, the particle can be used in the reverse as a "synthetic vaccine," by placing a CD14 protein on the particle, where the protein is non-specific or where it is a CD14 protein from a specific antigenic stimulation. The CD14 protein on the particle will stimulate monocytes in circulation to attack a target. If a non-specific CD14 protein is placed on the particles, then the monocytes will convert into macrophages and attack anything the body deems foreign. If a specific CD14 protein is placed on the particle, the monocytes will convert into macrophages and attack whatever the CD14 target is. So, the particle can be used by binding a CD14 antibody to the particle to remove a target (as showed in FIGS. 13, 14, and 15) or by binding a CD14 protein to the particle to stimulate agents in circulation to act against a target.

h. Example 8: Capture of Canine Heartworm Microfilaria by Nanodiamonds/Particles without Agents Currently, detection of blood parasites (e.g., canine heartworm microfilariae) is performed using current antibody diagnostic identification methodologies. For detection of the parasites in the blood using these methodologies, the parasites are coated in some way with the antibodies that are then detected via the methodologies. However, for reasons not yet fully understood, the body does not or cannot actively destroy and remove the parasites. It was theorized that the particles of the invention, once functionalized, could be used to capture and hold parasites for removal.

Steps performed include the following:
1) Ordered Heartworm microfilaria canine whole blood.
2) Functionalized nanodiamonds according to the methods described above, but with a few variations, including the following:
   a. Place and keep nanodiamonds in the hypertonic solution for over 3 weeks. This 3-week duration was used initially as a test of the duration of functionalization and possible hold time from functionalization.
   b. Removed nanodiamonds from the hypertonic saline. The conjugation steps were not performed, and the nanodiamonds were left unconjugated (i.e., no antibody or other agent was attached).
3) Placed nanodiamonds with ½ cc whole blood mixed for approximately 1 minute.
4) Placed sample on slide for visualization.
5) Used a light microscope to visualize sample to verify that the particles did indeed capture the parasites (microfilaria). The parasites already had antibodies present on them, since the antibodies had been placed there by the body. Verified capture of the parasites in the blood by the unconjugated nanodiamonds.

6) Verified strength of the bonding by creating a vortex action on the slide while being directly visualized. The microfilaria was not removed from the particles via slide vortex.

This Example illustrates the capture of targets by the particles themselves (e.g., by the binding sites exposed on the nanodiamonds via the functionalization process described above), rather than by agents, such as antibodies. The results showed that over approximately 99% of the microfilariae present on the slide were captured and held by the unconjugated nanodiamonds (or by binding sites on the nanodiamonds). The nanodiamonds captured the parasites possibly by capturing antibodies attached to the parasites themselves or by binding a protein coat of the parasites. The nanodiamonds bound the parasites without prior conjugation of the particles with antibodies/antigens, or other agents that might do the capture. One microfilaria was seen as being without particle. It may have had extremely small particles attached, but sufficient fluorescent capability was not available to confirm or deny this. Interestingly, it was noted that 100% of the microfilaria body itself was not bound, but the body appeared to be tightly bound in sections. This was noted based on free flowing areas of RBCs and particles on the microfilaria body during the vortex. If the nanodiamonds bound antibodies on the parasites (as opposed to a protein coat or other protein of the parasite), these may be areas of the microfilaria body that are not coated with antibody and may be part of the mechanism used by the microfilaria to elude the body naturally, when the body is infected with such parasites. The invention can thus be used to capture blood parasites, including capture of forms of malaria, leishmaniasis, etc.

Figure 16:
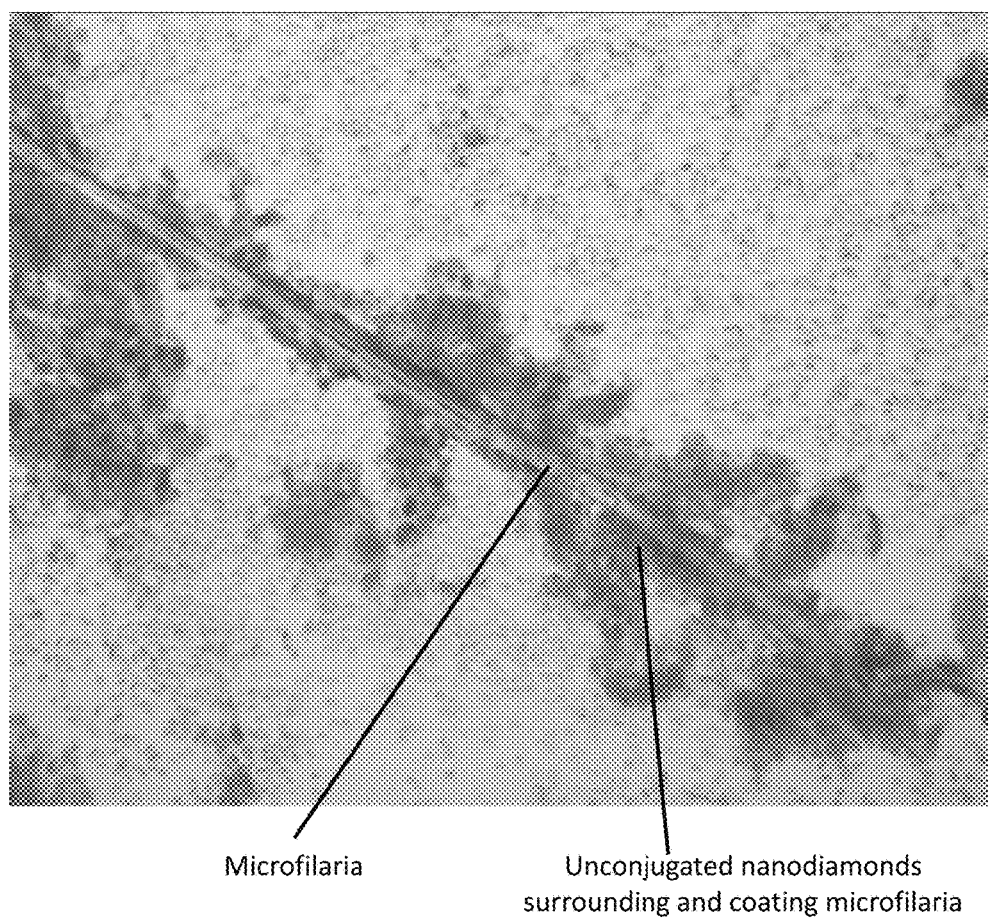
FIG. 16 is a light micrograph of unconjugated nanodiamonds surrounding and coating canine heartworm microfilaria (parasite), according to an embodiment of the invention.

In a second experiment, the steps described above were performed again. This time the nanodiamonds were functionalized in 1NHCL, and then were washed three times in hypertonic saline rinse to a pH of approximately 5-6. Again, no antibodies or other agents were complexed with the nanodiamond, so nanodiamond remained unconjugated to attempt to determine if the functionalized nanodiamond would itself attach to/conjugate to the parasitic organism. FIG. 16 is a light micrograph illustrating the results of this second experiment. FIG. 16 shows canine heartworm microfilaria surrounded/coated by functionalized, unconjugated nanodiamonds, indicating that the nanodiamonds (or nanodiamond binding sites) interacted with the parasite without antibodies or other agents being attached to the nanodiamonds.

While the invention has been particularly shown and described with reference to a preferred embodiment and various alternate embodiments, it will be understood by persons skilled in the relevant art that various changes in form and details can be made therein without departing from the spirit and scope of the invention. The description has been presented for the purpose of illustration; it is not intended to be exhaustive or to limit the invention to the precise forms disclosed. Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein. It must be noted that, as used in the specification, the singular forms "a," "an" and "the" include plural referents unless the context clearly dictates otherwise.

All references, issued patents and patent applications cited within the body of the instant specification are hereby incorporated by reference in their entirety, for all purposes.

REFERENCES CITED

1. Luminex corporation at Luminex.com
2. Luminex Corporation 2009 Earnings Report and Balance Sheet 2009 at http://phx.corporateir.net/phoenix.zhtml?c=79403&p=irolnewsArticle&ID=1383385&hig hlight=; downloaded 8 Mar. 2010
3. Lote, K. (1981). Temporary Ischaemia Induced by Degradable Starch Microspheres: Possible thrombogenic effects in vivo and in vitro. *Acta Oncologica,* 20(2), 91-96. doi:10.3109/02841868109130426.
4. Yewdell, J W., Frank, E., Gerhard W (1981). *Expression of influenza A virus internal antigens on the surface of infected P*815 *cells* The Journal of Immunology, Vol 126, Issue 5 1814-1819
5. Howard R J. (1984). *Antigenic variation of bloodstage malaria parasites.* Philos Trans R Soc Lond B Biol Sci. 1984 Nov. 13; 307(1131):141-58.
6. Egilmez, N., Jong, Y., Mathiowitz, E. Bankert R. *Tumor Vaccination with Cytokine-Encapsulated Microspheres* (2002). Lung Cancer: Volume 2: *Diagnostic and Therapeutic Methods and Reviews* Methods in Molecular Medicine Vol 75 Pg: 687-696 DOI: 10.1385/1-59259-324-0:687
7. Davis, I. D. (2000) *An overview of cancer immunotherapy. Immunol. Cell Biol.* 78, 179-195.
8. Minev, B. R., Chavez, F. L., and Mitchell, M. S. (1999) *Cancer Vaccines: Novel approaches and new promise.* Pharmacol. Ther. 81(2), 121-139.
9. Gansbacher, B., Bannerji, R., Daniels, B. Zier, K., Cronin, K., and Gilboa, E. (1990) *Retroviral vector-mediated gamma-interferon gene transfer into tumor cells generates potent and long-lasting anti-tumor immunity.* Cancer Res. 50, 7820-7825.
10. Sabel, M. S., Hill, H., Jong, Y. S., Mathiowitz, E., Bankert, R. B., and Egilmez, N. K. (2001) *Neoadjuvant therapy with IL-*12-*loaded PLA microspheres reduces local recurrence and distant metastases.* Surgery 130(3), 470-478.
11. Egilmez, N. K., Jong, Y. S., Hess, S. D., Jacob, J. S., Mathiowitz, E., and Bankert, R. B. (2000) *Cytokines delivered by biodegradable microspheres promote effective suppression of human tumors by human peripheral blood lymphocytes in the SCID/Winn model.* J. Immunother. 23, 190-195.
12. Tamion F, Richard V, Lyoumi S, Daveau M, Bonmarchand G, Leroy J, Thuillez C, Lebreton J P (1997).: *Gut ischemia and mesenteric synthesis of inflammatory cytokines after hemorrhagic or endotoxic shock.* Am J Physiol. August; 273(2 Pt 1):G314-21.
13. Sato H, Tanaka T, Kita T, Yamaguchi H, Tanaka N. (2004): *The role of tumour necrosis factor-alpha in renal dysfunction following mild haemorrhage in rats.* Int J Exp Pathol. December; 85(6):345-53.

14. Whiteley W, Jackson C, Lewis S, Lowe G, Rumley A, Sandercock P, Wardlaw J, Dennis M, Sudlow C.: *Inflammatory markers and poor outcome after stroke: a prospective cohort study and systematic review of interleukin-6.* PLoS Med. 2009 September; 6(9):e1000145. Epub 2009 Sep. 8.
15. *NINDS Guillain-Barré Syndrome Information Page*: http://www.ninds.nih.gov/disorders/gbs/gbs.htm—downloaded 8 Mar. 2010
16. Kulin, S., Kishore, R, Hubbard, J. B. and Helmerson, K (2002): *Real-Time Measurement of Spontaneous Antigen-Antibody Dissociation* Biophysical Journal Volume 83 October pg. 1965-1973
17. Bradac, C., Gaebel, T., Naidoo, N., et al. (2009): *Prediction and measurement of the size-dependent stability of fluorescence in diamond over the entire nanoscale* Nano Letters Vol 9, No. 10 pg. 3555-3564
18. Neugart, F, Zappe, A., Jelezko, F., Tietz, C., et al. (2007): *Dynamics of diamond nanoparticles in solution and cells* Nano Letters Vol. 7 No. 12 pg 3588-3591
19. Greiner, N. R, Philips, D. S., Johnson, J. D. Volk, F (1988) Nature 333, 440-442
20. Huang, H., Pierstorff, E., Osawa, E., Ho, D. (2007): *Active nanodiamond hydrogels for chemotherapeutic delivery* Nano Letters Vol. 7, No. 11 pg. 3305-3314
21. Schrand, A. M.; Huang, H.; Carlson, C.; Schlager, J. J.; Ōsawa, E.; Hussain, S. M.; Dai, L. (2007); *Are diamond nanoparticles cytotoxic?*, J. Phys. Chem. B., 111[1], 2-7.
22. Leonard, S. (2009) *Electrically Conductive Diamond Shows Promise for In Vivo MEMS Devices* October Medical Product Manufacturing News www.devicelink.com/mpmn/archive/09/10/002.html: downloaded 16 Mar. 2010
23. Schrand, A.; Ciftan, S.; Hens, C.; Shenderova, O. (2009) *Nanodiamond Particles: Properties and Perspectives for Bioapplications* Critical Reviews in Solid State and Materials Sciences, 34:18-74
24. BBC News Online 1 Nov. 2010 Last updated at 21:17 ET *Jellyfish cells 'diagnose' cancer, York scientists say*, BBC News, http://www.bbc.co.uk/news/uk-england-york-north-yorkshire-11667447.
25. Mohan N, Chen C S, Hsieh H H, Wu Y C, Chang H C. *In vivo imaging and toxicity assessments of fluorescent nanodiamonds in Caenorhabditis elegans*. Nano Lett. Sep. 8 2010; 10(9):3692-3699.
26. Vandelinger V. and Groisman A., *Perfusion in Microfluidic Cross-Flow: Separation of White Blood Cells from Whole Blood and Exchange of Medium in a Continuous Flow*, Anal. Chem. 79(5): 202-203 (2007).
27. Putney S. and Burke P., *Improving protein therapeutics with sustained-release formulations*, Nature Biotec. 16, 153-157 (1998).
28. Yang K., et al., *Preparation of DNA-encapsulated polyethersulfone hollow microspheres for organic compounds and heavy metal ions removal*, Desalination, 175 (3), pp. 297-302 (30 May 2005).

The invention claimed is:

1. An external immune apparatus, comprising a container holding a plurality of particles that have been functionalized to expose one or more binding sites for presentation to a body fluid, wherein the container is configured for receiving the body fluid through a first line, the body fluid received passing through the container holding the particles, and wherein one or more agents bound by the binding sites of the particles are presented to the body fluid for binding targets within the body fluid as the body fluid passes across the particles and for forming an agent-target complex that exits the container through a second line.

2. The apparatus of claim 1, wherein the particles are nanodiamonds.

3. The apparatus of claim 1, wherein the container is attached to one of the first line and the second line, which are attached to a body for binding targets within the body fluid from the body in real time.

4. The apparatus of claim 1, wherein the body fluid is blood, wherein the container is attached to one of the first line and the second line, and wherein the first line and the second line are intravenous lines attached to a body for delivering blood to the container and for receiving blood from the container.

5. The apparatus of claim 1, wherein the container is a removable cartridge that is insertable into or attachable to one or both of the first and second line, which are attached to an intravenous bag.

6. The apparatus of claim 1, wherein the one or more agents bound by binding sites exposed on the functionalized particles bind the targets in the body fluid as the body fluid passes across the particles, wherein the one or more agents are presentation agents.

7. The apparatus of claim 1, wherein the agents presented to the body fluid expose the body fluid to the agents to provide vaccination to the body fluid.

8. The apparatus of claim 1, wherein the agents presented to the body fluid expose the body fluid to the agents to produce an immune response in the body fluid.

9. The apparatus of claim 1, wherein the agents are antibodies or antigens.

10. The apparatus of claim 1, wherein the agents include a first agent that has captured a second agent, wherein the second agent captures the targets or wherein the second agent is presented to the body fluid.

11. The apparatus of claim 1, wherein the agents include monocyte-differentiation antigen antibodies, and wherein the targets are cells that are engulfed by macrophages in the body fluid.

12. The apparatus of claim 1, wherein the agents remain functional once bound by the particles.

13. The apparatus of claim 1, wherein the targets remain functional once bound by the agents.

14. The apparatus of claim 1, wherein the targets are selected from a group consisting of: parasites, cytokines, antigens, antibodies, viruses, bacteria, pathogens, endotoxins, genetic material, and cells.

15. The apparatus of claim 1, wherein a second container is configured to be placed in sequence after the container, such that a first line of the second container connects to the second line of the container.

16. The apparatus of claim 15, wherein the second container in sequence is configured to be flushed with a solution.

17. The apparatus of claim 1, wherein the container is configured to be flushed with a solution that releases the agent-target complex from the particles, thus allowing the particles to remain in the container as the agent-target complex exits the container through the second line.

18. The apparatus of claim 1, wherein the container comprises one or more injection ports, each injection port configured for injecting materials into the container.

19. The apparatus of claim 1, wherein the container comprises one or more injection ports, each injection port configured for withdrawing materials from the container.

20. The apparatus of claim 1, wherein the one or more agents bound by the binding sites of the particles are presented to the body fluid for binding targets within the body fluid as the body fluid passes across the particles and for forming the agent-target complex that exits the container through the second line in a first use, and, in a second use, the one or more agents bound by the binding sites of the particles are capable of binding targets in the body fluid for filtering out the targets from the body fluid as the body fluid passes across the particles to produce filtered body fluid that exits the container through the second line.

* * * * *